United States Patent
Okumura et al.

(10) Patent No.: US 8,134,027 B2
(45) Date of Patent: Mar. 13, 2012

(54) SULFONYLIMIDE SALT AND METHOD FOR PRODUCING THE SAME

(75) Inventors: Yasunori Okumura, Kobe (JP); Kazuo Takei, Suita (JP); Shimpei Sato, Takatsuki (JP); Yuichi Sato, Takatsuki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/935,410

(22) PCT Filed: Mar. 30, 2009

(86) PCT No.: PCT/JP2009/057010
§ 371 (c)(1),
(2), (4) Date: Sep. 29, 2010

(87) PCT Pub. No.: WO2009/123328
PCT Pub. Date: Oct. 8, 2009

(65) Prior Publication Data
US 2011/0034716 A1   Feb. 10, 2011

(30) Foreign Application Priority Data

Mar. 31, 2008  (JP) ................................. 2008-093240
Jan. 22, 2009  (JP) ................................. 2009-012344
Jan. 22, 2009  (JP) ................................. 2009-012345
Jan. 22, 2009  (JP) ................................. 2009-012346

(51) Int. Cl.
*C07C 303/00*   (2006.01)
(52) U.S. Cl. ....................................................... 564/83
(58) Field of Classification Search ...................... 564/83
See application file for complete search history.

(56) References Cited

U.S. PATENT DOCUMENTS

| 5,916,475 | A | 6/1999 | Michot et al. |
| 6,254,797 | B1 | 7/2001 | Michot et al. |
| 7,253,317 | B2 | 8/2007 | Cernik et al. |
| 7,439,395 | B2 * | 10/2008 | Ignatyev et al. ............... 564/232 |
| 7,605,271 | B2 * | 10/2009 | Uchimura et al. .......... 548/300.1 |
| 2004/0097757 | A1 | 5/2004 | Cernik et al. |

FOREIGN PATENT DOCUMENTS

| JP | 8-511274 | 11/1996 |
| JP | 2004-522681 | 7/2004 |
| JP | 2005-200359 | 7/2005 |
| JP | 2006-210331 | 8/2006 |
| JP | 2007-182410 | 7/2007 |

OTHER PUBLICATIONS

International Search Report issued Jun. 23, 2009 in International (PCT) Application No. PCT/JP2009/057010.
PCT Written Opinion of the International Searching Authority issued Jun. 23, 2009 in International (PCT) Application No. PCT/JP2009/057010.
Ruff et al., "Imidodisulfuryl Fluoride, Cesium Imidodisulfuryl Fluoride, and Fluoroimidodisulfuryl Fluoride", Inorganic Syntheses, pp. 138-143 (1968).
Krumm et al., "Synthesis of Poly- and the First Perfluoroalkyl-N(SO$_2$F)$_2$ Derivatives: Improved Methods for the Preparation of XN(SO$_2$F)$_2$ (X=H, Cl) and Single-Crystal Diffraction Studies of HN(SO$_2$Cl)$_2$, HN(SO$_2$F)$_2$, and CF$_3$CH$_2$N(SO$_2$F)$_2$" Inorg. Chem. vol. 37, pp. 6295-6303 (1998).
Singh et al., "Bis(fluorosulphuryl)imide Derivatives of Zinc(II), Cadmium(II), Mercury(II) and Their Coordination Complexes with Oxygen and Nitrogen Donors" Indian Journal of Chemistry, vol. 28A, No. 10, pp. 890-892 (1989).
Ruff, "The Imidodisulfuryl Fluoride Ion" Inorganic Chemistry, vol. 4, No. 10, pp. 1446-1449 (1965).
Beran et al., "A New Method of the Preparation of Imido-bis(sulfuric acid) Dihalogenide, (F,Cl), and the Potassium Salt of Imido-bis-(sulfuric acid) Difluoride" Z. Anorg. Allg. Chem. vol. 631, pp. 55-59 (2005).
Supplementary European Search Report issued Apr. 15, 2011 in corresponding European Application No. 09 72 7567.
H.W. Roesky et al. "Darstellung von N-Trifluorrnethansulfonyl-sulfonylfluoridamid und einige Reaktionen", Inorganic and Nuclear Chemistry Letters, vol. 7, No. 2, 1971, pp. 171-175 (with English translation).
Database Reaxys [Online] Elsevier Properties, FR: XP-002630635., Jul. 2005.

* cited by examiner

*Primary Examiner* — Jafar Parsa
(74) *Attorney, Agent, or Firm* — Wenderoth, Lind & Ponack, L.L.P.

(57) ABSTRACT

The present invention provides a method for producing fluorosulfonylimides more safely, rapidly and efficiently, which enables suppression of production of by-products, and fluorosulfonylimides. The method for producing a fluorosulfonylimide salt of the present invention includes a step of reacting a fluoride compound containing at least one element selected from the group consisting of elements of Group 11 to Group 15 and Period 4 to Period 6 (excluding arsenic and antimony) with a compound represented by the following general formula (I) to give a fluorosulfonylimide salt represented by the general formula (II):
[Chemical Formula 1]

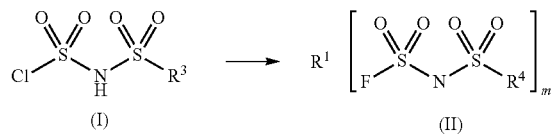

wherein $R^1$ denotes at least one element selected from the group consisting of elements of Group 11 to Group 15 and Period 4 to Period 6 (excluding arsenic and antimony); $R^3$ denotes fluorine, chlorine or a fluorinated alkyl group having 1 to 6 carbon atoms; $R^4$ denotes fluorine or a fluorinated alkyl group having 1 to 6 carbon atoms; and m denotes an integer of 2 or 3.

19 Claims, No Drawings

SULFONYLIMIDE SALT AND METHOD FOR PRODUCING THE SAME

TECHNICAL FIELD

The present invention relates to fluorosulfonylimides, and more particularly to N-(fluorosulfonyl)-N-(fluoroalkylsulfonyl)imide, di(fluorosulfonyl)imide and a derivative thereof such as a salt thereof, and a method for producing the same.

BACKGROUND ART

Fluorosulfonylimides such as N-(fluorosulfonyl)-N-(fluoroalkylsulfonyl)imide and di(fluorosulfonyl)imide, and derivatives thereof are useful as intermediates for compounds having a $N(SO_2F)$ group or an $N(SO_2F)_2$ group, and are also useful compounds in various applications, for example, electrolytes, additives for electrolytic solutions of fuel cells, selective electrophilic fluorinating agents, photo acid generators, thermal acid generators, and near infrared light-absorbing dyes.

Di(fluorosulfonyl)imides described above have conventionally been prepared by a halogen exchange reaction of di(chlorosulfonyl)imide using a fluorinating agent. For example, arsenic trifluoride ($AsF_3$) is used as a fluorinating agent in Non-patent Document 1 (John K. Ruff and Max Lustig, Inorg Synth. 11, 138-140 (1968)) and antimony trifluoride ($SbF_3$) is used as a fluorinating agent in Non-patent Document 2 (Jean'ne M. Shreeve et al., Inorg. Chem. 1998, 37(24), 6295-6303). Patent Document 1 (Japanese Published Patent Publication No. 2004-522681) describes a method in which di(chlorosulfonyl)imide is fluorinated using an ionic fluoride of monovalent cations, such as KF or CsF as a fluorinating agent. Also, Patent Document 2 (Japanese Published Patent Publication No. H08-511274) discloses a method in which di(fluorosulfonyl)imide is prepared by distilling fluorosulfonic acid ($HFSO_3$) in the presence of urea.

DISCLOSURE OF THE INVENTION

However, when $AsF_3$ is used as the fluorinating agent, there are problems that it is difficult to avoid the generation of by-products, which are not easily separated from the product, and that $AsF_3$ is comparatively expensive. Although a problem of by-products can be solved by using $SbF_3$ in place of $AsF_3$, both As and Sb are elements having high toxicity and therefore it is desired to avoid using them as much as possible. According to the method described in Patent Document 2, hydrogen fluoride is produced during the reaction. Since hydrogen fluoride is a substance having strong toxicity and corrosiveness, when the product contains hydrogen fluoride, not only a reaction apparatus but also peripheral members may be corroded when the di(fluorosulfonyl)imide is used as a salt in various applications. Furthermore, the method described in Patent Document 1 has a problem that the reaction requires a long time.

Under these circumstances, the present invention has been made and an object thereof is to provide a method for producing fluorosulfonylimides such as N-(fluorosulfonyl)-N-(fluoroalkylsulfonyl)imide, di(fluorosulfonyl)imide and salts thereof more safely, rapidly and efficiently, which enables suppression of production of by-products, and to provide fluorosulfonylimides.

The production method of the present invention which has solved the above problems is a method for producing a fluorosulfonylimide salt, which comprises reacting a fluoride compound containing at least one element selected from the group consisting of elements of Group 11 to Group 15 and Period 4 to Period 6 (excluding arsenic and antimony) with a compound represented by the following general formula (I) to obtain a fluorosulfonylimide salt represented by the general formula (II):

[Chemical Formula 1]

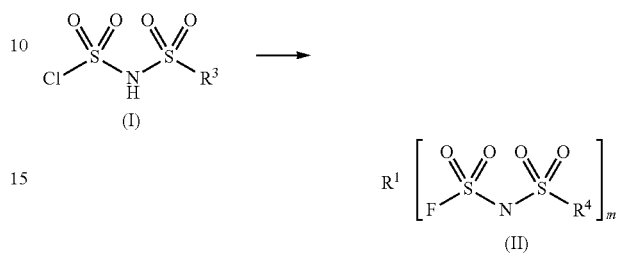

wherein $R^1$ denotes at least one element selected from the group consisting of elements of Group 11 to Group 15 and Period 4 to Period 6 (excluding arsenic and antimony); $R^3$ denotes fluorine, chlorine or a fluorinated alkyl group having 1 to 6 carbon atoms; $R^4$ denotes fluorine or a fluorinated alkyl group having 1 to 6 carbon atoms; and m denotes an integer of 2 or 3.

In addition, the present invention also has a feature in that it comprises steps of: reacting a compound represented by the general formula (I) shown in the following scheme with an onium salt to give an organic salt of chlorosulfonylimide represented by the general formula (VIII); and reacting the onium salt of chlorosulfonylimide with a fluoride compound containing at least one element selected from the group consisting of elements of Group 11 to Group 15 and Period 4 to Period 6 (excluding arsenic and antimony) to obtain a compound represented by the general formula (VI), in this order:

[Chemical Formula 2]

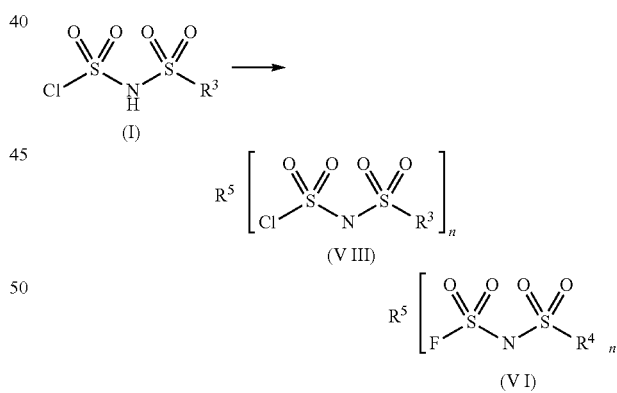

wherein, in the formula (I) and the formula (VIII), $R^3$ denotes fluorine, chlorine or a fluorinated alkyl group having 1 to 6 carbon atoms; $R^4$ in the formula (VI) denotes fluorine or a fluorinated alkyl group; $R^5$ in the formula (VIII) and the formula (VI) denotes an onium cation; and n corresponds to a valence of the onium cation $R^5$ and denotes an integer of 1 to 3.

The term "fluorosulfonylimide" in the present invention includes, in addition to di(fluorosulfonyl)imide having two fluorosulfonyl groups, N-(fluorosulfonyl)-N-(fluoroalkylsulfonyl)imide having a fluorosulfonyl group and a fluorinated alkyl group. The term "chlorosulfonylimide" is the same. The term "fluoroalkyl" means an alkyl group having 1 to 6 carbon atoms in which one or more hydrogen atoms are substituted with fluorine atoms and includes, for example, a fluoromethyl group, a difluoromethyl group, a trifluoromethyl group, a fluoroethyl group, a difluoroethyl group, a trifluoroethyl group and a pentafluoroethyl group.

BEST MODE FOR CARRYING OUT THE INVENTION

The method of the present invention has a feature in that a fluoride compound containing at least one element selected from the group consisting of elements of Group 11 to Group 15 and Period 4 to Period 6 (excluding arsenic and antimony) is employed. Therefore, the present invention encompasses any methods including a step for fluorination of chlorosulfonylimides by employing the fluoride compound. Specifically, as a preferable present methods of the present invention, the method for reacting a fluoride compound containing at least one element selected from the group consisting of elements of Group 11 to Group 15 and Period 4 to Period 6 (excluding arsenic and antimony) with chlorosulfonylimide; and the method for reacting the fluoride compound with a chlorosulfonylimide salt are exemplified. Hereinafter, the present methods will be described in detail.

The present invention is a method for producing a fluorosulfonylimide salt such as a di(fluorosulfonyl)imide salt or an N-(fluorosulfonyl)-N-(fluoroalkylsulfonyl)imide salt and has a feature in that a fluoride compound containing at least one element selected from the group consisting of elements of Group 11 to Group 15 and Period 4 to Period 6 (excluding arsenic and antimony) is reacted with a compound represented by the following general formula (I) to obtain a fluorosulfonylimide salt represented by the general formula (II).
[Chemical Formula 3]

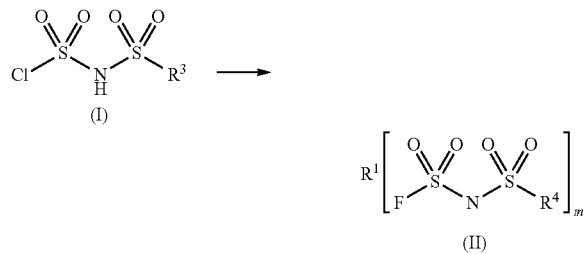

In the above general formula, $R^1$ denotes at least one element selected from the group consisting of elements of Group 11 to Group 15 and Period 4 to Period 6 (excluding arsenic and antimony); $R^3$ denotes fluorine, chlorine or a fluorinated alkyl group having 1 to 6 carbon atoms; $R^4$ denotes fluorine or a fluorinated alkyl group having 1 to 6 carbon atoms; and m denotes an integer of 2 or 3.

In the following, the method of the present invention will be described in detail. First, in the method of the present invention, the compound represented by the general formula (I) is reacted with a fluoride to obtain a fluorosulfonylimide salt (reaction intermediate) represented by the general formula (II).

Examples of the compound represented by the general formula (I) include a compound in which $R^3$ is fluorine (F), chlorine (Cl) or a fluorinated alkyl group having 1 to 6 carbon atoms. The fluorinated alkyl group preferably has 1 to 6 carbon atoms, and more preferably 1 to 4 carbon atoms. Specific examples of the fluorinated alkyl group having 1 to 6 carbon atoms include a fluoromethyl group, a difluoromethyl group, a trifluoromethyl group, a fluoroethyl group, a difluoroethyl group, a 2,2,2-trifluoroethyl group, a pentafluoroethyl group, a 3,3,3-trifluoropropyl group, a perfluoro-n-propyl group, a fluoropropyl group, a perfluoroisopropyl group, a fluorobutyl group, a 3,3,4,4,4-pentafluorobutyl group, a perfluoro-n-butyl group, a perfluoroisobutyl group, a perfluoro-t-butyl group, a perfluoro-sec-butyl group, a fluoropentyl group, a perfluoropentyl group, a perfluoroisopentyl group, a perfluoro-t-pentyl group, a fluorohexyl group, a perfluoro-n-hexyl group and a perfluoroisohexyl group. Among these groups, a trifluoromethyl group, a pentafluoroethyl group and a perfluoro-n-propyl group are preferred, and a trifluoromethyl group and a pentafluoroethyl group are more preferred.

As the compound represented by the general formula (I), a commercially available compound may be used, but it can also be synthesized using cyanogen chloride (CNCl) as a starting material (refer to the following scheme).
[Chemical Formula 4]

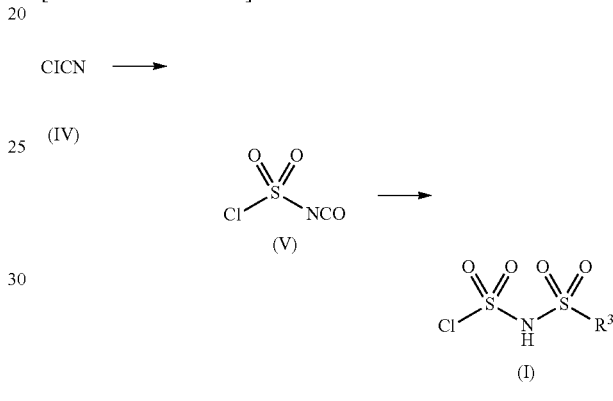

In the formula, $R^3$ denotes fluorine, chlorine or a fluorinated alkyl group having 1 to 6 carbon atoms.

For example, when di(chlorosulfonyl)imide is synthesized, cyanogen chloride may be reacted with sulfuric anhydride ($SO_3$) and chlorosulfonic acid. In this case, first, cyanogen chloride is reacted with sulfuric anhydride (compound (IV)→compound (V)). The ratio of these starting materials is preferably from 1:0.5 to 1:10 (cyanogen chloride:sulfuric anhydride, molar ratio), and more preferably from 1:1 to 1:5.

The conditions in the case of reacting cyanogen chloride with sulfuric anhydride are not particularly limited and can be appropriately adjusted according to the progress of the reaction. For example, the reaction temperature is preferably adjusted within a range from 0° C. to 100° C. (more preferably from 10° C. to 50° C.) and the reaction time is preferably adjusted within a range from 0.1 hour to 48 hours (more preferably from 1 hour to 24 hours). The reaction is preferably carried out without using a solvent, but a solvent may be used as necessary. An aprotic solvent described hereinafter is preferably used as the solvent.

Next, the resulting chlorosulfonyl isocyanate ($ClSO_2NCO$, the formula (V) shown above) is reacted with chlorosulfonic acid to obtain di(chlorosulfonyl)imide (the formula (I) shown above, $R^3$ is Cl). The ratio of chlorosulfonyl isocyanate (compound (V)) to chlorosulfonic acid is preferably adjusted within a range from 1:0.5 to 1:2 (chlorosulfonyl isocyanate chlorosulfonic acid, molar ratio), and more preferably from 1:0.8 to 1:1.2.

The reaction of chlorosulfonyl isocyanate with chlorosulfonic acid may be carried out under an inert gas atmosphere at 50° C. to 200° C. (more preferably 70° C. to 180° C.) for 0.1 hour to 48 hours (more preferably 1 hour to 24 hours).

Although the chlorosulfonic acid is in liquid form and therefore can function as a reaction solvent during the synthesis reaction, other solvents may be used as necessary.

N-(chlorosulfonyl)-N-(fluoroalkylsulfonyl)imide of the above formula (I) in which $R^3$ is a fluorinated alkyl group having 1 to 6 carbon atoms is obtained by the reaction of chlorosulfonyl isocyanate with fluorinated alkyl sulfonic acid, or the reaction of fluorinated alkyl sulfonyl isocyanate with chlorosulfonic acid. The fluorinated alkyl sulfonic acid is preferably trifluoromethanesulfonic acid.

The mixing ratio of chlorosulfonyl isocyanate (compound (V)) to fluorinated alkyl sulfonic acid is preferably adjusted within a range from 1:0.5 to 1:2 (chlorosulfonyl isocyanate:fluoroalkyl compound, molar ratio), and more preferably from 1:0.8 to 1:1.2. As the reaction conditions, the same conditions as those in the case of synthesizing di(chlorosulfonyl)imide can be employed.

N-(chlorosulfonyl)-N-(fluorosulfonyl)imide of the above formula (I) in which $R^3$ is fluorine is obtained by the reaction of chlorosulfonyl isocyanate with fluorosulfonic acid, or the reaction of fluorosulfonyl isocyanate and chlorosulfonic acid. The amount of starting materials and the reaction conditions to be employed may be the same as those in the case of di(chlorosulfonyl)imide.

Furthermore, the di(chlorosulfonyl)imide is synthesized by reacting amidosulfuric acid with thionyl chloride and reacting the product with chlorosulfonic acid (for example, refer to Z. Anorg. Allg. Chem 2005, 631, 55-59).
[Chemical Formula 5]

The ratio of amidosulfuric acid to thionyl chloride is preferably adjusted within a range from 1:1 to 1:20 (amidosulfuric acid:thionyl chloride, molar ratio), and more preferably from 1:2 to 1:10. The ratio of chlorosulfonic acid to amidosulfuric acid is preferably adjusted within a range from 1:0.5 to 1:10 (amidosulfuric acid:chlorosulfonic acid, molar ratio), and more preferably from 1:1 to 1:5.

The conditions in the case of reacting amidosulfuric acid with thionyl chloride and chlorosulfonic acid are not particularly limited and may be appropriately adjusted according to the progress of the reaction. For example, the reaction temperature is preferably adjusted within a range from 0° C. to 200° C., and more preferably from 50° C. to 150° C. Alternatively, the reaction may be carried out while stepwisely increasing the temperature within the above temperature range. The reaction time is preferably adjusted within a range from 0.1 hour to 100 hours, and more preferably from 1 to 50 hours. Although the reaction is preferably carried out without using a solvent, a solvent may be used as necessary.

Next, the resulting chlorosulfonylimide (compound (I)) is reacted with a fluoride compound containing at least one element selected from the group consisting of elements of Group 11 to Group 15 and Period 4 to Period 6 (excluding arsenic and antimony) (compound (I)→compound (II)). The fluoride compound preferably contains an element capable of being converted into a di- or higher polyvalent cation among the above elements. Specifically, the element is preferably an element capable of being converted into a divalent cation, such as Cu, Zn, Sn or Pb, and an element capable of being converted into a trivalent cation, such as Bi. The fluoride compound is preferably $CuF_2$, $ZnF_2$, $SnF_2$, $PbF_2$ or $BiF_3$, more preferably $CuF_2$, $ZnF_2$ or $BiF_3$, and still more preferably $ZnF_2$.

By using the above fluoride compound, each exchange reaction of halogen (chlorine→fluorine) and proton (H→$R^1$) of the compound (I) can be carried out in a one step. Therefore, when the method of the present invention is employed, a desired salt can be rapidly obtained without using a complicated process. By preliminarily replacing the proton of the compound (I) with the above element, it becomes easy to perform a purification operation when compared with the case where the proton is not exchanged. Therefore, it can be said that any method including the step of reacting a fluoride compound containing at least one element selected from the group consisting of elements of Group 11 to Group 15 and Period 4 to Period 6 (excluding arsenic and antimony) with a compound represented by the above general formula (I) is a preferred embodiment of the present invention.

The compound represented by the formula (II) is a reaction intermediate of a di(fluorosulfonyl)imide salt or an N-(fluorosulfonyl)-N-(fluoroalkylsulfonyl)imide salt represented by the formula (III), and the intermediate is also useful as an electrolyte for a lithium secondary battery and a capacitor, and as an intermediate of derivatives of fluorosulfonyl imide.

The mixing ratio of the compound represented by the general formula (I) to the fluoride compound is preferably adjusted within a range from 1:0.8 to 1:10 (compound (I):fluoride compound, molar ratio), more preferably from 1:1 to 1:5, and still more preferably from 1:1 to 1:2, when di(chlorosulfonyl)imide (compound (I)) is reacted with a divalent fluoride. When a trivalent fluoride compound is employed, the mixing ratio is preferably adjusted within a range from 1:0.5 to 1:7, more preferably from 1:0.7 to 1:3, and still more preferably from 1:0.7 to 1:1.3. In contrast, when N-(chlorosulfonyl)-N-(fluoroalkylsulfonyl)imide or N-(chlorosulfonyl)-N-(fluorosulfonyl)imide is used as the compound (I), the mixing ratio in the case of reacting with a divalent fluoride (compound (I):fluoride compound, molar ratio) is preferably adjusted within a range from 1:0.4 to 1:5, more preferably from 1:0.5 to 1:2.5, and still more preferably from 1:0.5 to 1:1. When reacted with a trivalent fluoride, the mixing ratio is preferably adjusted within a range from 1:0.3 to 1:3, more preferably from 1:0.3 to 1:0.8, and still more preferably from 1:0.3 to 1:0.7.

The reaction conditions in the case of obtaining the compound (II) from the compound (I) may be appropriately adjusted according to the progress of the reaction. It is recommended that the reaction temperature is adjusted within a range from 0° C. to 200° C. (more preferably 10° C. to 100° C.) and the reaction time is adjusted within a range from 0.1 hour to 48 hours (more preferably 1 hour to 24 hours).

When starting materials are in liquid form and are dissolved with each other, it is not necessarily required to use a reaction solvent, but an aprotic solvent is preferably used, for example. Specific examples of the reaction solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene. In view of smooth proceeding of the fluorination reaction, it is recommended to use a polar solvent. Among the solvents exemplified above, valeronitrile, ethyl acetate, isopropyl acetate and butyl acetate are preferred. In view of operability upon purification, a solvent having a low boiling point and capable of forming a two-layered state with water is preferred.

Next, the resulting compound (II) is cationically exchanged to change $R^1$ into $R^2$, thus obtaining a compound (III) (the following formula (III)). That is, the method including the step of cationically exchanging the compound (II) to obtain the compound (III) of the present invention is also shown be following.
[Chemical Formula 6]

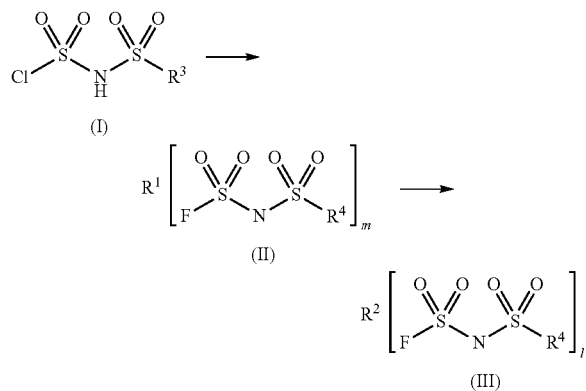

In the formula (III), $R^2$ denotes $H^+$ or a metal ion other than $R^1$, $R^2$ is preferably an alkali metal such as Li, Na, K, Rb or Cs, and Li is more preferable among the alkali metal. $R^4$ denotes fluorine or a fluorinated alkyl group having 1 to 6 carbon atoms. Alkali metal salts of di(fluorosulfonyl)imide and N-(fluorosulfonyl)-N-(fluoroalkylsulfonyl)imide can be used as an electrolyte for a lithium secondary battery or a capacitor.

Examples of the method of the cation exchange reaction from the compound (II) into the compound (III) include a method of reacting a salt containing a desired cation with the compound (II) and a method of contacting the compound (II) with a cation-exchange resin. Examples of the compound (salt), which gives a compound (III) in which $R^2$ is $H^+$ or an alkali metal, include sulfonates such as fluorosulfonic acid, chlorosulfonic acid, methanesulfonic acid and trifluoromethanesulfonic acid; hydroxides such as sulfuric acid, LiOH, NaOH, KOH, RbOH and CsOH; carbonates such as $Na_2CO_3$, $K_2CO_3$, $Rb_2CO_3$ and $Cs_2CO_3$; hydrogen carbonates such as $LiHCO_3$, $NaHCO_3$, $KHCO_3$, $RbHCO_3$ and $CsHCO_3$; chlorides such as LiCl, NaCl, KCl, RbCl and CsCl; fluorides such as LiF, NaF, KF, RbF and CsF; alkoxide compounds such $CH_3OLi$ and $Et_2OLi$; alkali metal salts such as alkyllithium compounds (EtLi, BuLi and t-BuLi (Et denotes an ethyl group and Bu denotes a butyl group)).

At this time, a solvent may be used as necessary and preferred examples of the solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene. In view of operability upon purification, a solvent having a low boiling point and capable of forming a two-layered state with water is preferred. Among the solvents exemplified above, valeronitrile, ethyl acetate, isopropyl acetate and butyl acetate are preferred.

The mixing ratio of the compound (II) to the sulfonate, sulfuric acid or alkali metal salt is preferably adjusted within a range from 1:2 to 1:20 (compound (II):salt, molar ratio), more preferably from 1:2 to 1:10, and still more preferably from 1:2 to 1:4, when the compound (II) has a divalent cation, a desired cation is a monovalent cation and the compound (II) is mixed with a salt containing the desired monovalent cation. When the compound (II) has a divalent cation, a desired cation is a divalent cation and the compound (II) is mixed with a salt containing the desired divalent cation, the mixing ratio is preferably adjusted within a range from 1:1 to 1:10, more preferably from 1:1 to 1:5, and still more preferably from 1:1 to 1:2. On the other hand, when the compound (II) has a trivalent cation, a desired cation is a monovalent cation and the compound (II) is mixed with a salt containing the desired monovalent cation, the mixing ratio is preferably adjusted within a range from 1:3 to 1:30, more preferably from 1:3 to 1:15, and still more preferably from 1:3 to 1:6. Also, when the compound (II) has a trivalent cation, a desired cation is a divalent cation and the compound (II) is mixed with a salt containing the desired divalent cation, the mixing ratio is preferably adjusted within a range from 1:1 to 1:20, more preferably from 1:1 to 1:10, and still more preferably from 1:2 to 1:4.

Although there is no imitation on the reaction time and the reaction temperature, it is recommended that the reaction temperature is adjusted within a range from 0° C. to 200° C. (more preferably from 10° C. to 100° C.) and the reaction time is adjusted within a range from 0.1 hour to 48 hours (more preferably from 1 hour to 24 hours).

The cation-exchange resin to be used is preferably a strongly acidic cation-exchange resin. The developing solvent includes, for example, water.

When a cation-exchange resin is used, first, a cation of the cation-exchange resin is substituted with a desired cation by a known method and, after filling a column with the substituted cation-exchange resin, an aqueous solution prepared by dissolving the compound of the formula (II) in water is passed through the column to obtain an aqueous solution containing the compound of the formula (III) in which $R^1$ is replaced by a desired cation $R^2$.

When $R^2$ is $H^+$ in the formula (III), by reacting the compound (III) with hydroxides such as LiOH, NaOH, KOH, RbOH and CsOH; carbonates such as $Na_2CO_3$, $K_2CO_3$, $Rb_2CO_3$ and $Cs_2CO_3$; hydrogen carbonates such as $LiHCO_3$, $NaHCO_3$, $KHCO_3$, $RbHCO_3$ and $CsHCO_3$; chlorides such as LiCl, NaCl, KCl, RbCl and CsCl; fluorides such as LiF, NaF, KF, RbF and CsF; alkoxide compounds such as $CH_3OLi$ and $Et_2OLi$; and alkyllithium compounds such as EtLi, BuLi and t-BuLi (Et denotes an ethyl group, and Bu denotes a butyl group), a salt of the compound (III) containing an alkali metal as a cation is obtained (an exchange reaction from a proton into an alkali metal).

The mixing ratio of the compound (III) to the monovalent alkali metal salt is preferably adjusted within a range from 1:1 to 1:10 (compound (III):alkali metal salt, molar ratio), and more preferably from 1:1 to 1:2. When a divalent alkali metal salt is employed, the mixing ratio is preferably within a range from 1:1 to 1:5, and more preferably from 1:1 to 1:2.

In the case of the cation-exchange reaction of the compound (III), a solvent may be used as necessary. Examples of the preferably usable solvents include aprotic solvents such as ethylene carbonate, propylene carbonate, butylene carbonate, γ-butyrolactone, γ-valerolactone, dimethoxymethane, 1,2- dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene.

By reacting fluorosulfonylimide salts represented by the formula (II) or (III) with a suitable salt, it is possible to change a cation represented by $R^1$ in the formula (II) or a cation represented by $R^2$ in the formula (III) with a cation contained in the suitable salt. When used as a material of an ion conductor of an electrochemical device, the cation is preferably an organic cation (the following formula (VI)).

[Chemical Formula 7]

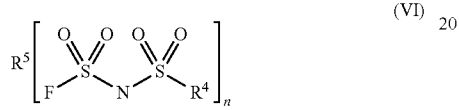
(VI)

In the formula (VI), $R^4$ denotes fluorine or a fluorinated alkyl group having 1 to 6 carbon atoms; $R^5$ denotes an organic cation; and n corresponds to a valence of an organic cation $R^5$ and denotes an integer of 1 to 3.

The organic cation $R^5$ constituting an organic salt of fluorosulfonylimide represented by the formula (VI) is preferably an onium cation. A fluorosulfonylimide salt containing an onium cation becomes an ambient temperature molten salt capable of stably maintaining a molten state at ambient temperature, and is suited for use as a material of an ion conductor of an electrochemical device, which can withstand for use over a long period of time.

The onium cation is preferably an onium cation represented by the following general formula (VII);

[Chemical Formula 8]

$$L^{\oplus}\text{-Rs} \quad (VII)$$

wherein L denotes C, Si, N, P, S or O; R are the same or different and denote hydrogen or organic groups, or may be combined with each other; s denotes 2, 3 or 4 and is a value depending on a valence of an element L; and an L—R bond may be a single bond or a double bond. Specifically, the onium cation is preferably an onium cation represented by the following general formula:

[Chemical Formula 9]

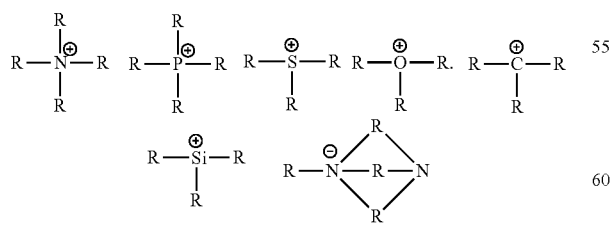

wherein R denotes the same as in the general formula (VII). These onium cations may be employed alone, or two or more kinds of them may be employed in combination. Among these, the following onium cations (1) to (4) are preferred.

(1) One among nine kinds of heterocyclic onium cations represented by the following general formulas:

[Chemical Formula 10]

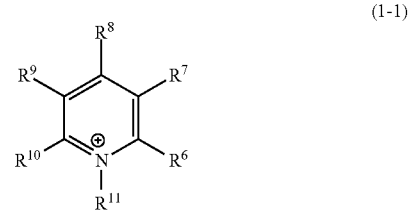
(1-1)

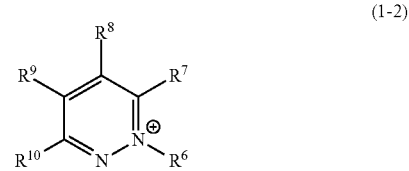
(1-2)

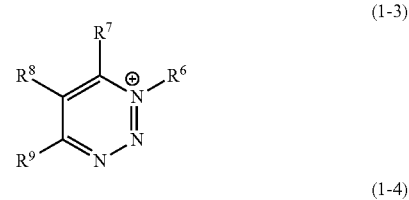
(1-3)

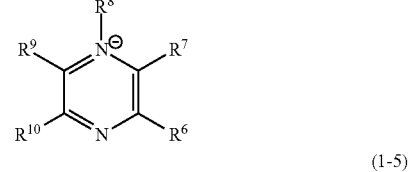
(1-4)

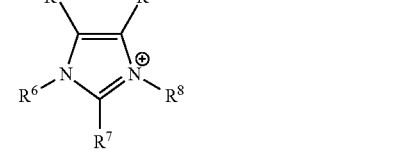
(1-5)

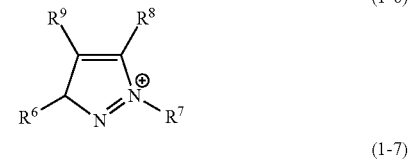
(1-6)

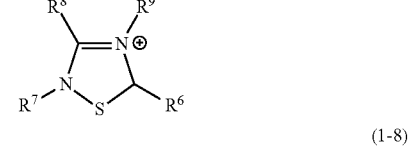
(1-7)

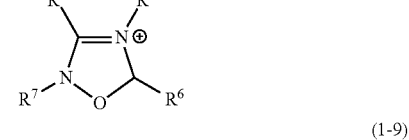
(1-8)

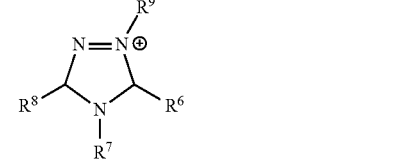
(1-9)

(2) One among five kinds of unsaturated onium cations represented by the following general formulas:

[Chemical Formula 11]

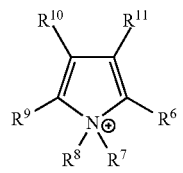
(2-1)

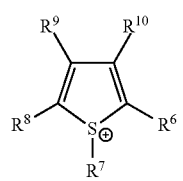
(2-2)

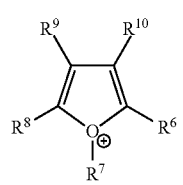
(2-3)

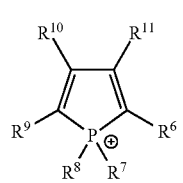
(2-4)

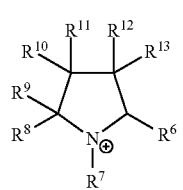
(2-5)

(3) One among ten kinds of saturated cyclic onium cations represented by the following general formulas:

[Chemical Formula 12]

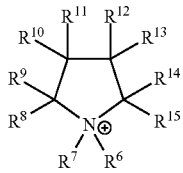
(3-1)

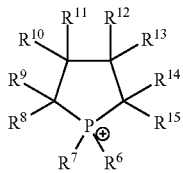
(3-2)

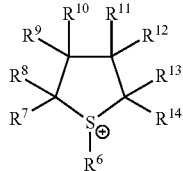
(3-3)

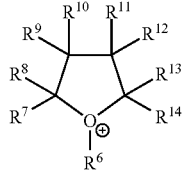
(3-4)

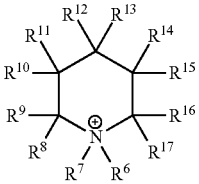
(3-5)

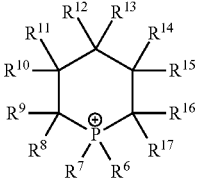
(3-6)

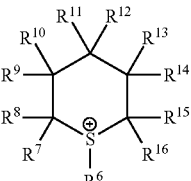
(3-7)

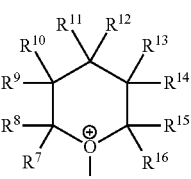
(3-8)

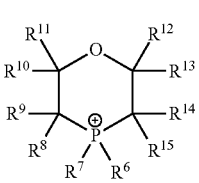
(3-9)

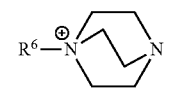
(3-10)

In the above general formulas, $R^6$ to $R^{17}$ denote organic groups and they are the same or different and may be bonded to each other.

(4) A chain onium cation in which R is hydrogen or an alkyl group having 1 to 8 carbon atoms. Among these onium cations, preferred is an onium cation of the general formula (VII) in which L is N. Examples thereof include quaternary ammoniums such as tetramethylammonium, tetraethylammonium, tetrapropylammonium, tetrabutylammonium, tetraheptylammonium, tetrahexylammonium, tetraoctylammonium, triethylmethylammonium, methoxyethyldiethylmethylammonium, trimethylphenylammonium, benzyltrimethylammonium, benzyltributylammonium, benzyltriethylammonium, dimethyldistearylammonium, diallyldimethylammonium, 2-methoxyethoxymethyltrimethylammonium and tetrakis(pentafluoroethyl)ammonium; tertiary ammoniums such as trimethylammonium, triethylammonium, tributylammonium, diethylmethylammonium, dimethylethylammonium and dibutylmethylammonium; secondary ammoniums such as dimethylammonium, diethylammonium and dibutylammonium; primary ammoniums such as methylammonium, ethylammonium, butylammonium, hexylammonium and octylammonium; and ammonium compounds such as N-methoxytrimethylammonium, N-ethoxytrimethylammonium, N-propoxytrimethylammonium and $NH_4$. Among these chain onium cations, ammonium, trimethylammonium, triethylammonium, tributylammonium, triethylmethylammonium, tetraethylammonium and diethylmethyl(2-methoxyethyl)ammonium are preferable chain onium cations.

Among the onium cations (1) to (4), five kinds of onium cations represented by the following general formula:
[Chemical Formula 13]

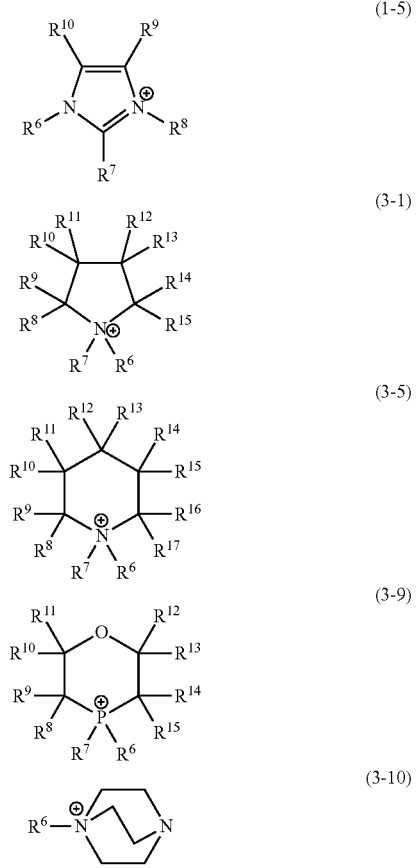

wherein $R^6$ to $R^{17}$ are as defined above, and the chain onium cation (4) are preferred. The organic group of $R^6$ to $R^{17}$ is preferably a linear, branched or cyclic saturated or unsaturated hydrocarbon group having 1 to 18 carbon atoms or a fluorocarbon group, and more preferably a saturated or unsaturated hydrocarbon group having 1 to 8 carbon atoms or a fluorocarbon group. These organic groups may contain a hydrogen atom, a fluorine atom, a nitrogen atom, an oxygen atom, a sulfur atom, or a functional group such as an amino group, an imino group, an amide group, an ether group, an ester group, a hydroxyl group, a carboxyl group, a carbamoyl group, a cyano group, a sulfone group or a sulfide group. More preferably, the organic group has one or more of a hydrogen atom, a fluorine atom, a cyano group, a sulfone group and the like. When two or more organic groups are bonded to each other, the bond may be formed between main skeletons of the organic groups, between the main skeleton of the organic group and the above functional group, or between the functional groups.

The onium cation is derived from a salt of the onium cation and an anion. Examples of the anion of the salt containing the onium cation include fluorine, chlorine, bromine, iodine, a hydroxide ion ($OH^-$), a carbonate ion and a hydrogen carbonate ion.

When the organic salt of fluorosulfonylimides of the present invention is obtained, the ratio of fluorosulfonylimide salts represented by the formula (II) or (III) to the salt containing the onium cation is preferably adjusted within a range from 1:0.5 to 1:10 (molar ratio), and more preferably from 1:1 to 1:5, when the cation of the fluorosulfonylimide salts (II) or (III) is monovalent. When the cation of the fluorosulfonylimide salts (II) or (III) is divalent, the ratio is preferably adjusted within a range from 1:1 to 1:20 (molar ratio), and more preferably from 1:2 to 1:10. When the cation is trivalent, the ratio is preferably adjusted within a range from 1:1.5 to 1:30 (molar ratio), and more preferably from 1:3 to 1:15.

The cation exchange reaction into the organic cation is carried out by mixing fluorosulfonylimide salts with a salt containing the onium cation in the presence of a solvent. The reaction may be carried out at the temperature of 0° C. to 200° C. (more preferably 10° C. to 100° C.) for 0.1 hour to 48 hours (more preferably 0.1 hour to 24 hours).

As a solvent, for example, aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene are preferably used. In view of operability upon purification, a solvent having a low boiling point and capable of forming a two-layered state with water is preferred. Among the solvents exemplified above, valeronitrile, ethyl acetate, isopropyl acetate and butyl acetate are preferred by the following reason. That is, metal salts produced as by-products can be efficiently removed by using these solvents.

While the method including fluorinating chlorosulfonylimide (I) to obtain a fluorosulfonylimide salt (II) and performing a cation exchange reaction of the resulting salt to obtain a fluorosulfonylimide salt (III) or (VI) was described, the timing of the fluorination reaction is not particularly limited in the present invention and the fluorination reaction may be carried out after preliminarily exchanging a cation of chlorosulfonylimide (I) into an organic salt such as an onium salt. As described above, by exchanging chlorosulfonylimides into an onium salt prior to fluorination of Cl, heat generation upon the fluorination reaction can be suppressed as compared with the case of having a proton, that is, the case of an imide compound as it is. It is noted that the gist of the present invention is employing the fluoride compound. That is, the present invention encompasses any methods including a step for fluorination of chlorosulfonylimides by using the fluoride compound.

Hereinafter, the present method in which a cation exchange reaction is carried out prior to a fluorination of chlorosulfonylimides is described. The present method in which the cation exchange reaction is carried out prior to fluorination has a feature in that it includes steps of: reacting a compound represented by the general formula (I) shown in the following scheme with an onium salt to obtain an organic salt of chlorosulfonylimide represented by the general formula (VIII); and reacting the organic salt (VIII) of chlorosulfonylimide with a fluoride compound containing at least one element selected from the group consisting of elements of Group 11 to Group 15 and Period 4 to Period 6 (excluding arsenic and antimony) to obtain a compound represented by the general formula (VI), in this order.

[Chemical Formula 14]

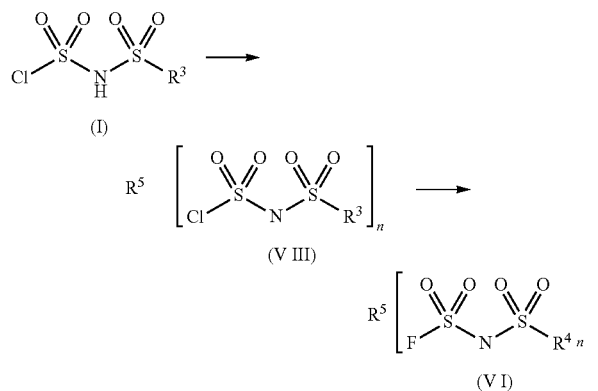

In the above scheme, $R^3$ denotes fluorine (F), chlorine (Cl) or a fluorinated alkyl group having 1 to 6 carbon atoms; $R^4$ denotes fluorine or a fluorinated alkyl group; $R^5$ denotes an onium cation; and n corresponds to a valence of an onium cation $R^5$ and denotes an integer of 1 to 3.

In this method, first, a compound represented by the general formula (I) in the above scheme is reacted with an onium salt to obtain a compound represented by the general formula (VIII) (organic salt of chlorosulfonylimide). The onium salts described above can be employed as the onium salt.

In the cation exchange reaction from the compound (I) to the compound (VIII) of the above scheme, the mixing ratio of the compound represented by the general formula (I) to the onium salt is preferably adjusted within a range from 1:0.5 to 1:10 (molar ratio), and more preferably from 1:1 to 1:5. The reaction of exchange from the proton into the onium cation is carried out by mixing chlorosulfonylimides represented by the general formula (I) with the onium salt in the presence of a solvent. The reaction may be carried out at a temperature of 0° C. to 200° C. (more preferably 1° C. to 100° C.) for 0.1 hour to 48 hours (more preferably 0.1 hour to 24 hours).

Examples of the usable solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene. In view of operability upon purification, a solvent having a low boiling point and capable of forming a two-layered state with water is preferred. Among the solvents exemplified above, valeronitrile, ethyl acetate, isopropyl acetate and butyl acetate are preferred.

Subsequently, the resulting organic salt of chlorosulfonylimide represented by the general formula (VIII) is reacted with a fluoride compound containing at least one element selected from the group consisting of elements of Group 11 to Group 15 and Period 4 to Period 6 (excluding arsenic and antimony) to obtain a compound represented by the general formula (VI) (compound (VIII)→compound (VI)).

The same fluoride compound as described above can be employed as the fluoride compound. The mixing ratio of the organic salt of chlorosulfonylimide represented by the general formula (VIII) to the fluoride compound is preferably adjusted within a range from 1:0.8 to 1:10 (compound (VIII): fluoride, molar ratio), more preferably from 1:1 to 1:5, and still more preferably from 1:1 to 1:2, when di(chlorosulfonyl) imide (compound (VIII)) is reacted with a divalent fluoride compound. When reacted with a trivalent fluoride compound, the mixing ratio is preferably adjusted within a range from 1:0.5 to 1:7, more preferably from 1:0.7 to 1:3, and still more preferably from 1:0.7 to 1:1.3. On the other hand, when N-(chlorosulfonyl)-N-(fluoroalkylsulfonyl)imide or N-(fluorosulfonyl)-N-(chlorosulfonyl)imide is employed as the compound (VIII), the mixing ratio in the case of reacting with a divalent fluoride compound is preferably adjusted within a range from 1:0.4 to 1:5 (compound (VIII):fluoride compound, molar ratio), more preferably from 1:0.5 to 1:2.5, and still more preferably from 1:0.5 to 1:1. When reacted with a trivalent fluoride, the mixing ratio is preferably adjusted within a range from 1:0.3 to 1:3, more preferably 1:0.3 to 1:0.8, and still more preferably from 1:0.3 to 1:0.7 by the following reason. That is, when the amount of the fluoride compound is too small, the unreacted chloro compound may be remained. In contrast, when the amount of the fluoride is too large, it becomes difficult to remove the unreacted raw material.

The reaction conditions in the case of obtaining a compound (VI) from a compound (VIII) are appropriately adjusted according to the progress of the reaction. It is recommended that the reaction temperature is adjusted within a range from 0° C. to 200° C. (more preferably from 10° C. to 100° C.) and the reaction time is adjusted within a range from 0.1 hour to 48 hours (more preferably from 1 to 24 hours).

When starting materials are in liquid form and are dissolved with each other, it is not necessarily required to use a reaction solvent, but an aprotic solvent such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane or nitrobenzene is preferably used. In view of smooth proceeding of the fluorination reaction, it is recommended to use a polar solvent. Among the above mentioned aprotic solvents, valeronitrile, ethyl acetate, isopropyl acetate and butyl acetate are preferred since metal salts produced as by-products are efficiently removed by using these solvents.

In view of operability upon purification, a solvent having a low boiling point and capable of forming a two-layered state with water is preferred.

An organic salt (VI) of di(fluorosulfonyl)imide or of N-(fluorosulfonyl)-N-(fluoroalkylsulfonyl)imide obtained by the present method becomes an ambient temperature molten salt capable of stably maintaining a molten state at ambient temperature (for example, being in a liquid state at 100° C. or lower) and is useful as a material of an ion conductor of an electrochemical device, which can withstand for use over a long period of time, namely, an electrolyte for a lithium secondary battery or a capacitor.

The organic salt of fluorosulfonylimide represented by the general formula (VI) may be reacted with an alkali metal compound, and thus an organic cation $R^5$ can also be cationically exchanged into an alkali metal. Thereby, a compound (III) is obtained. As described above, the alkali metal salt of fluorosulfonylimide can be obtained by a cation exchange reaction of a compound (II), and can also be obtained by cationically exchanging a fluorosulfonylimide salt (II) to obtain an organic salt (VI) of fluorosulfonylimide and then performing a cation exchange reaction, as shown in the following scheme.

[Chemical Formula 15]

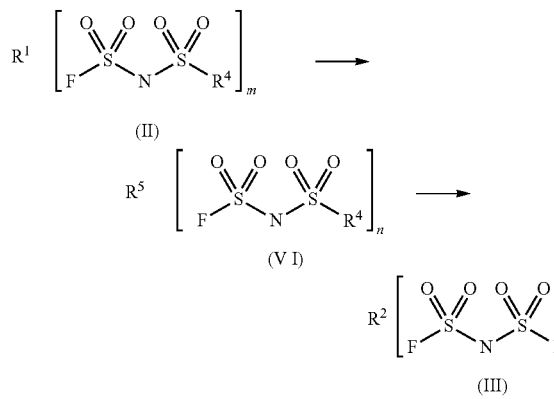

Examples of the method of the cation exchange reaction from a compound (VI) into a compound (III) include a method of reacting a salt containing a desired alkali metal ion with a compound (VI) and a method of contacting a compound (VI) with a cation-exchange resin. It is also possible to obtain fluorosulfonylimide in which $R^2$ is $H^+$ by reacting a compound (VI) with a suitable salt.

Examples of the compound (salt) having an alkali metal as $R^2$ which gives a compound (III) include hydroxides such as LiOH, NaOH, KOH, RbOH and CsOH; carbonates such as $Na_2CO_3$, $K_2CO_3$, $Rb_2CO_3$ and $Cs_2CO_3$ hydrogen carbonates such as $LiHCO_3$, $NaHCO_3$, $KHCO_3$, $RbHCO_3$ and $CsHCO_3$; chlorides such as LiCl, NaCl, KCl, RbCl and CsCl; fluorides such as LiF, NaF, KF, RbF and CsF; alkoxide compounds such as $CH_3OLi$ and $Et_2OLi$; and alkyllithium compounds such as EtLi, BuLi and t-BuLi.

At this time, a solvent may be used as necessary and preferred examples of the solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene. Since these solvents are the same as those used in the step of obtaining a compound (VI), it is possible to proceed to the step of obtaining a compound (III) without changing a reaction solvent after the production of a compound (VI).

The mixing ratio of the compound (VI) to the alkali metal salt is preferably adjusted within a range from 1:1 to 1:10 (compound (VI):salt, molar ratio), more preferably from 1:1 to 1:5, and still more preferably from 1:1 to 1:3, when an onium cation $R^5$ of the compound (VI) is monovalent.

Although there is no particular limitation on the reaction time and the reaction temperature, it is recommended that the reaction temperature is adjusted within a range from 0° C. to 200° C. (more preferably from 10° C. to 100° C.) and the reaction time is adjusted within a range from 0.1 hour to 48 hours (more preferably from 1 hour to 24 hours).

After the reaction, the product may be purified so as to enhance purity. In the present invention, the objective product can be easily purified by a separation and extraction method using water, an organic solvent and a mixed solvent of these. Examples of organic solvents usable in the purification process include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethylmethyl carbonate, diethyl carbonate, acetonitrile, sulfolane, 3-methylsulfolane, dimethyl sulfoxide, N,N-dimethylformamide, N-methyloxazolidinone, valeronitrile, benzonitrile, ethyl acetate, isopropyl acetate, butyl acetate, nitromethane and nitrobenzene. As a matter of course, conventionally known purification methods such as a method of washing with the above solvent, a reprecipitation method, a separation and extraction method, a recrystallization method, a crystallization method and a purification method by chromatography may be employed.

Di(fluorosulfonyl)imide and N-(fluorosulfonyl)-N-(fluoroalkylsulfonyl)imide obtained by the method of the present invention, and a salt thereof, and a reaction intermediate thereof are useful as an electrolyte for a lithium secondary battery or a capacitor, and as an intermediate derivatives of fluorosulfonyl imide. The organic salt of di(fluorosulfonyl)imide or N-(fluorosulfonyl)-N-(fluoroalkylsulfonyl)imide of the present invention is suited for use as a material of an ion conductor constituting electrochemical devices such as a primary battery, batteries having a charge/discharge mechanism, such as a lithium (ion) secondary battery and a fuel cell, an electrolytic capacitor, an electric double layer capacitor, a solar battery and an electrochromic display device.

When a di(fluorosulfonyl)imide salt or an N-(fluorosulfonyl)-N-(fluoroalkylsulfonyl)imide salt of the present invention is used as a material for an electrolytic solution, the electrolytic solution further containing an alkali metal salt and/or an alkali earth metal salt is preferred. In this case, the alkali metal salt and/or the alkali earth metal salt may be a compound containing di(fluorosulfonyl)imide or N-(fluorosulfonyl)-N-(fluoroalkylsulfonyl)imide of the present invention as an anion (compound represented by the above formula (III)), or a compound which does not contain di(fluorosulfonyl)imide or N-(fluorosulfonyl)-N-(fluoroalkylsulfonyl)imide of the present invention and. The material for an electrolytic solution containing the alkali metal salt and/or the alkali earth metal salt contains an electrolyte and is therefore suited for use as a material of an electrolytic solution of an electrochemical device.

A lithium salt, a sodium salt and a potassium salt are preferred as the alkali metal salt, and a calcium salt and a magnesium salt are preferred as the alkali earth metal salt. A lithium salt is more preferred.

EXAMPLES

The present invention is more specifically described by the following examples. It is to be understood that the present invention is not limited to the examples, and various appropriate variations made in accordance with the purports described hereinbefore and hereinafter are also included in the technical scope of the present invention.

Synthesis Example 1

Synthesis of Chlorosulfonyl Isocyanate

In a 200 ml reaction vessel equipped with a stirrer, a thermometer, a reflux apparatus and a gas introducing tube, 80.1 g (1.0 mol) of liquid sulfuric anhydride ($SO_3$) was charged and 61.5 g (0.53 mol) of a cyanogen chloride gas (CNCl) was introduced at a temperature of 25° C. to 35° C. over 2 hours, and the temperature of the reaction solution was adjusted to 25° C. to 30° C., followed by stirring for 0.5 hour. After completion of the reaction, the reflux apparatus and the gas introducing tube were removed from the reaction vessel, followed by distillation under a normal pressure to obtain a colorless transparent liquid: 83.7%) as a fraction at 106° C. to 107° C. (yield (amount): 118.5 g, 0.83 mol, yield (percentage).

Synthesis Example 2

Synthesis of Di(chlorosulfonyl)imide

In a 500 ml reaction vessel equipped with a stirrer, a thermometer, a reflux apparatus and a dropping device, 148.7 g (1.28 mol) of chlorosulfonic acid ($ClSO_3H$) was added, followed by heating to 120° C. Then, 180.4 g (1.27 mol) of chlorosulfonyl isocyanate obtained in the same manner as in Synthesis Example 1 was added to the reaction vessel from the dropping device over 2 hours and the mixed solution was heated to 150° C., followed by stirring for 6 hours. After completion of the reaction, the reflux tube and the dropping device were removed from the reaction vessel, followed by distillation under reduced pressure to obtain a colorless transparent liquid as a fraction at 104° C. to 106° C. (0.3 kPa) (yield (amount): 178.4 g, 0.83 mol, yield (percentage): 65.6%).

Compound identification was carried out by IR (Varian 2000 FT-IR, manufactured by Varian, Inc., liquid membrane technique) and it was confirmed that the resulting colorless transparent liquid was di(chlorosulfonyl)imide.
IR (neat): vs (N—H) 3155, vas (S—O) 1433, 1428, vs (S—O) 1183, vs (N—S) 824 $cm^{-1}$

Synthesis Example 3

Synthesis of Bis[di(fluorosulfonyl)imide]zinc salt

In a 20 ml reaction vessel, 2.18 g (0.01 mol) of di(chlorosulfonyl)imide and 4.36 g of acetonitrile were added, followed by stirring. Into the reaction vessel, 2.63 g (0.025 mol) of $ZnF_2$ (Zinc fluoride) was added, followed by conducting a reaction at room temperature (25° C.) for 24 hours. The reaction solution was filtrated and the filtered material was washed with 5 g of acetonitrile, and then the solution prepared by combining the filtrate with the wash liquid was analyzed by $^{19}$F-NMR ("Unity plus, Model 400", manufactured by Varian, Inc., internal standard substance: trifluoromethylbenzene, integration time: 32). A peak area of the resulting chart was measured and the rate of conversion from chlorine into fluorine was determined and thus it was confirmed that the reaction quantitatively proceeded and a bis[di(fluorosulfonyl)imide]zinc salt was obtained.
$^{19}$F-NMR ($CD_3CN$): δ56.0

Synthesis Example 4

Synthesis of Bis[di(fluorosulfonyl)imide]zinc salt

In a 20 ml reaction vessel, 2.13 g (0.01 mol) of di(chlorosulfonyl)imide and 4.26 g of acetonitrile were charged, followed by stirring. Into the reaction vessel, 2.57 g (0.025 mol) of $ZnF_2$ was added, followed by conducting a reaction at room temperature (25° C.) for 1 hour. The reaction solution was filtrated and the filtered material was washed with 5 g of acetonitrile, and then the solution prepared by combining the filtrate with the wash liquid was analyzed by $^{19}$F-NMR in the same manner as in Synthesis Example 3. The results indicated that the reaction quantitatively proceeded and a bis[di(fluorosulfonyl)imide]zinc salt was obtained.
$^{19}$F-NMR ($CD_3CN$): δ56.0

Synthesis Example 5

Synthesis of Bis[di(fluorosulfonyl)imide]copper salt

In a 20 ml reaction vessel, 1.66 g (0.008 mol) of di(chlorosulfonyl)imide and 6.68 g of acetonitrile were charged, followed by stirring. Into the reaction vessel, 1.97 g (0.02 mol) of $CuF_2$ (Cupric fluoride) was added, followed by a reaction at room temperature (25° C.) for 24 hours. The reaction solution was filtrated and the filtered material was washed with 5 g of acetonitrile, and then the solution prepared by combining the filtrate with the wash liquid was analyzed by $^{19}$F-NMR in the same manner as in Synthesis Example 3. The results indicated that the reaction quantitatively proceeded and a bis[di(fluorosulfonyl)imide]copper salt was obtained.
$^{19}$F-NMR ($CD_3CN$): δ55.9

Synthesis Example 6

Synthesis of Tris[di(fluorosulfonyl)imide]bismuth salt

In a 20 ml reaction vessel, 2.46 g (10 mmol) of di(chlorosulfonyl)imide and 6.68 g of acetonitrile were charged, followed by stirring. Into the reaction vessel, 5.10 g (20 mmol) of $BiF_3$ (Bismuth (III) fluoride) was added, followed by conducting a reaction at room temperature (25° C.) for 24 hours. The reaction solution was filtrated and the filtered material was washed with 5 g of acetonitrile, and then the solution prepared by combining the filtrate with the wash liquid was analyzed by $^{19}$F-NMR in the same manner as in Synthesis Example 3. The results indicated that the reaction quantitatively proceeded and a tris[di(fluorosulfonyl)imide]bismuth salt was obtained.
$^{19}$F-NMR ($CD_3CN$): δ57.0

As is apparent from the results of Synthesis Examples 4 to 6, even when using a fluoride compound containing elements of Group 11 to Group 15 and Period 4 to Period 6 (excluding arsenic and antimony) other than Zn (Zinc), fluorination of chlorosulfonylimide rapidly proceeds and a fluorosulfonylimide salt can be efficiently obtained without generating by-products.

Synthesis Example 7

Synthesis of Bis[di(fluorosulfonyl)imide]zinc salt

In a 100 ml reaction vessel, 10.4 g (48.6 mmol) of di(chlorosulfonyl)imide and 20.8 g of acetonitrile were charged, followed by stirring. Into the reaction vessel, 12.5 g (120 mmol) of $ZnF_2$ was added, followed by conducting a reaction at room temperature (25° C.) for 24 hours. The reaction solution was filtered and the filtered material was washed with 25 g of acetonitrile, and then the solution prepared by combining the filtrate with the wash liquid was analyzed by $^{19}F$-NMR in the same manner as in Synthesis Example 3. The results indicated that the reaction quantitatively proceeded and a bis[di(fluorosulfonyl)imide]zinc salt was obtained.

Furthermore, acetonitrile was distilled off from the resulting solution and the solution was used as a starting material of Synthesis Example 8. $^{19}F$-NMR ($CD_3CN$): δ56.0

Synthesis Example 8

Synthesis of Di(fluorosulfonyl)imide lithium salt

A column having a volume of 100 ml (diameter: 2 cm) was filled with 36 g of a strongly acidic ion-exchange resin (Amberlite, Model IR-120B H, manufactured by ORGANO Corporation ("Amberlite" is a registered trademark of Rohm and Haas Company) and then filled with ion-exchange water. Then, an aqueous lithium hydroxide solution was added from the upper portion of the column and the aqueous solution was extracted from the lower portion of the column until the pH of the effluent became 10. Subsequently, ion-exchange water was added from the upper portion of the column and the aqueous solution was extracted from the lower portion of the column until the pH of the effluent became 7.

Then, an aqueous solution prepared by dissolving 2 g (4.7 mmol) of the bis[di(fluorosulfonyl)imide]zinc salt obtained in Synthesis Example 7 in 38 g of ion-exchange water was applied to the column, followed by outflow with ion-exchange water. X-ray fluorescence analysis (apparatus: PW-2404, manufactured by Philips) of the resulting aqueous solution revealed that an exchange reaction from zinc to lithium quantitatively proceeded and a di(fluorosulfonyl)imide lithium salt was obtained.

Comparative Synthesis Example 1

Synthesis of Di(fluorosulfonyl)imide

In a 20 ml reaction vessel, 3.09 g (14.4 mmol) of di(chlorosulfonyl)imide and 6.18 g of acetonitrile were charged, followed by stirring. Into the reaction vessel, 3.57 g (61.5 mmol) of potassium fluoride was added, followed by conducting a reaction at room temperature (25° C.) for 24 hours. The reaction solution was filtered and the filtered material was washed with 5 g of acetonitrile, and then the solution prepared by combining the filtrate with the wash liquid was analyzed by $^{19}F$-NMR in the same manner as in Synthesis Example 3. The results indicated that the rate of conversion from chlorine into fluorine was 3%, and most of the raw material was not fluorinated and remained as di(chlorosulfonyl)imide.

$^{19}F$-NMR ($CD_3CN$): δ55.9

Synthesis Example 9

Synthesis of Bis[di(fluorosulfonyl)imide]zinc salt

In a 20 ml reaction vessel, 1.80 g (0.008 mol) of di(chlorosulfonyl)imide and 3.59 g of acetonitrile were charged, followed by stirring. Into the reaction vessel, 0.87 g (0.008 mol) of $ZnF_2$ was added, followed by conducting a reaction at room temperature (25° C.) for 24 hours. Thereafter, the reaction solution was filtered and the filtered material was washed with 5 g of acetonitrile, and then the solution prepared by combining the filtrate with the wash liquid was analyzed by $^{19}F$-NMR in the same manner as in Synthesis Example 3. The results indicated that the reaction quantitatively proceeded and a bis[di(fluorosulfonyl)imide]zinc salt was obtained.

$^{19}F$-NMR ($CD_3CN$): δ56.0

Synthesis Example 10

Synthesis of Bis[di(fluorosulfonyl)imide]zinc salt

In a 100 ml reaction vessel, 54.39 g (0.25 mol) of di(chlorosulfonyl)imide and 108.9 g of acetonitrile were charged, followed by stirring. Into the reaction vessel, 26.27 g (0.25 mol) of $ZnF_2$ was added, followed by conducting a reaction at room temperature (25° C.) for 24 hours. Thereafter, the reaction solution was filtered and the filtered material was washed with 50 g of acetonitrile, and then the solution prepared by combining the filtrate with the wash liquid was analyzed by $^{19}F$-NMR in the same manner as in Synthesis Example 3. It was found that the reaction quantitatively proceeded and a bis[di(fluorosulfonyl)imide]zinc salt was obtained.

Acetonitrile was distilled off under reduced pressure from the solution prepared by combining the filtrate with the wash liquid to give 72.10 g of a solid (bis[di(fluorosulfonyl)imide] zinc salt).

$^{19}F$-NMR ($CD_3CN$): δ56.0

Synthesis Example 11

Synthesis of Ammonium salt of Di(fluorosulfonyl)imide

In a 100 ml reaction vessel, 5.05 g of the solid (bis[di (fluorosulfonyl)imide]zinc salt) obtained in Synthesis Example 10, 1.27 g (0.024 mol) of ammonium chloride as a compound containing an onium cation, 45 g of butyl acetate and 5 g of water were charged, followed by stirring at room temperature for 1 hour. The resulting solution was charged into a separatory funnel to separate an organic phase and the obtained organic phase was washed with 5 g of water. The washing operation was repeatedly carried out four times. Under reduced pressure, butyl acetate was distilled off from the resulting organic phase to obtain 1.53 g (0.0077 mol) of an ammonium salt of di(fluorosulfonyl)imide.

$^{19}F$-NMR ($CD_3CN$): δ56.0

Synthesis Example 12

Synthesis of Triethylammonium Salt of Di(fluorosulfonyl)imide

In a 100 ml reaction vessel, 5.08 g of the solid obtained in Synthesis Example 10, 3.29 g (0.024 mol) of triethylamine hydrochloride as a salt containing an onium cation, 45 g of butyl acetate and 5 g of water were charged, followed by stirring at room temperature for 1 hour. The resulting solution was charged into a separatory funnel to separate an organic phase and the obtained organic phase was washed with 5 g of water. The washing operation was repeatedly carried out four times. Under reduced pressure, butyl acetate was distilled off from the resulting organic phase to obtain 3.88 g (0.014 mol) of a triethylammonium salt of di(fluorosulfonyl)imide.

$^{19}$F-NMR (CD$_3$CN): δ55.9

Synthesis Example 13

Synthesis of Ethylmethylimidazolium Salt of Di(fluorosulfonyl)imide

In a 100 ml reaction vessel, 5.00 g of the solid obtained in Synthesis Example 10, 4.49 g (0.024 mol) of ethylmethylimidazolium bromide as a salt containing an onium cation, 45 g of butyl acetate and 5 g of water were charged, followed by stirring at room temperature for 1 hour. The resulting solution was charged into a separatory funnel to separate an organic phase and the obtained organic phase was washed with 5 g of water. The washing operation was repeatedly carried out four times. Under reduced pressure, butyl acetate was distilled off from the resulting organic phase to obtain 3.92 g (0.013 mol) of an ethylmethylimidazolium salt of di(fluorosulfonyl)imide.

$^{19}$F-NMR (CD$_3$CN): δ55.9

Synthesis Example 14

Synthesis of Bis[di(fluorosulfonyl)imide]zinc salt

In a 20 ml reaction vessel, 1.99 g (0.0093 mol) of di(chlorosulfonyl)imide and 3.98 g of butyl acetate were charged, followed by stirring. Into the reaction vessel, 0.96 g (0.0093 mol) of ZnF$_2$ was added, followed by conducting a reaction at room temperature (25° C.) for 24 hours. The resulting reaction solution was analyzed by $^{19}$F-NMR in the same manner as in Synthesis Example 3. It was found that the reaction quantitatively proceeded and a bis[di(fluorosulfonyl)imide]zinc salt was obtained.

$^{19}$F-NMR (CD$_3$CN): δ56.0

In Synthesis Example 14, butyl acetate was used as the solvent. Therefore, a cation exchange reaction for obtaining an onium salt could be carried out after the production of the bis[di(fluorosulfonyl)imide]zinc salt of Synthesis Example 14 without changing the solvent and carrying out a special purification treatment.

Synthesis Example 15

Synthesis of N-(chlorosulfonyl)-N-(trifluoromethylsulfonyl)imide

In a 500 ml reaction vessel equipped with a stirrer, a thermometer, a reflux apparatus and a dropping device, 190.6 g (1.27 mol) of trifluoromethanesulfonic acid (CF$_3$SO$_3$H) was charged, followed by heating to 120° C. After 179.7 g (1.27 mol) of chlorosulfonyl isocyanate obtained in the same manner as in Synthesis Example 1 was added to the reaction vessel from the dropping device over 2 hours, the mixed solution was heated to 150° C., followed by stirring for 6 hours. After completion of the reaction, the reflux apparatus and the dropping device were removed from the reaction vessel and distillation under reduced pressure was carried out to give a colorless transparent liquid (yield (amount): 212.9 g, 0.86 mol, yield (percentage): 67.7%).

From NMR analysis, it was found that the product was N-(chlorosulfonyl)-N-(trifluoromethylsulfonyl)imide.

Synthesis Example 16

Synthesis of Bis[N-(fluorosulfonyl)-N-(trifluoromethylsulfonyl)imide]zinc salt In a 20 ml reaction vessel, 2.00 g (8.1 mmol) of N-(chlorosulfonyl)-N-(trifluoromethylsulfonyl)imide obtained in Synthesis Example 15 and 18 g of butyl acetate were charged, followed by stirring. Into the reaction vessel, 0.44 g (4.3 mmol) of ZnF$_2$ was added, followed by a reaction at room temperature (25° C.) for 24 hours. The resulting reaction solution was filtered and then washed in the same manner as in Synthesis Example 3. $^{19}$F-NMR analysis of the solution prepared by combining the filtrate with the wash liquid indicated that the reaction quantitatively proceeded and a bis[N-(fluorosulfonyl)-N-(trifluoromethylsulfonyl)imide]zinc salt was obtained.

Synthesis Example 17

Synthesis Example 17-1

Synthesis of Bis[N-(fluorosulfonyl)-N-(trifluoromethylsulfonyl)imide]zinc salt In a 20 ml reaction vessel, 2.00 g (8.1 mmol) of N-(chlorosulfonyl)-N-(trifluoromethylsulfonyl)imide obtained in Synthesis Example 15 and 18 g of butyl acetate were charged, followed by stirring. Into the reaction vessel, 0.88 g (8.5 mmol) of ZnF$_2$ was added, followed by conducting a reaction at room temperature (25° C.) for 24 hours. The resulting reaction solution was filtered and washed in the same manner as in Synthesis Example 3, and then the solution prepared by combining the filtrate with the wash liquid was analyzed by $^{19}$F-NMR ("Model Unity plus 400", manufactured by Varian, Inc., internal standard substance: trifluoromethylbenzene, integration time: 32). A peak area of the resulting chart was measured and the rate of conversion from chlorine into fluorine was determined. Thus, the results indicated that the reaction quantitatively proceeded and a bis[N-(fluorosulfonyl)-N-(trifluoromethylsulfonyl)imide]zinc salt was obtained.

Synthesis Example 17-2

Synthesis of Onium Salt (Cation Exchange)

The resulting reaction solution was transferred to a 50 ml separatory funnel and an aqueous solution prepared by dissolving 1.7 g (12.4 mmol) of a hydrochloride of triethylamine in 1.2 g of distilled water was added and mixed, and then the aqueous phase was removed. Furthermore, 1.2 g of distilled water was added and mixed, and then the aqueous phase was removed. This liquid separating operation was repeatedly carried out four times. The resulting organic phase was dried to give an N-(fluorosulfonyl)-N-(trifluoromethylsulfonyl)

imidetriethylammonium salt (yield (amount): 1.44 g (4.3 mmol)). The obtained product was analyzed by $^{19}$F-NMR and $^{1}$H-NMR. ($^{19}$F-NMR (CD$_3$CN): δ56.0, $^{1}$H-NMR (CD$_3$CN): δ3.1 (6H), 1.2 (9H)).

Synthesis Example 17-3

Synthesis of Lithium Salt (Cation Exchange)

Furthermore, the resulting N-(fluorosulfonyl)-N-(trifluoromethylsulfonyl)imidetriethylammonium salt was transferred to a 50 ml separatory funnel and an aqueous solution prepared by dissolving 0.55 g (13.1 mmol) of lithium hydroxide monohydrate in 2.5 g of distilled water was added and mixed, and then the aqueous phase was removed by a liquid separating operation. The resulting organic phase was evaporated to dryness to obtain 0.83 g (3.5 mmol) of a lithium salt of N-(fluorosulfonyl)-N-(trifluoromethylsulfonyl)imide. Analysis by $^{19}$F-NMR and $^{1}$H-NMR indicated that the objective product was obtained since a peak attributed to triethylammonium disappeared.

Synthesis Example 18

Synthesis Example 18-1

Synthesis of Zinc Salt of Di(fluorosulfonyl)imide

In a 3 L reaction vessel, 240.00 g (1.12 mol) of di(chlorosulfonyl)imide and 2160 g of butyl acetate were charged, followed by stirring. Into the reaction vessel, 121.72 g (1.18 mol) of ZnF$_2$ was added, followed by a reaction at room temperature (25° C.) for 3 hours. The resulting reaction solution was filtered and washed in the same manner as in Synthesis Example 3, and then the solution prepared by combining the filtrate with the wash liquid was analyzed by $^{19}$F-NMR. Thus, the results indicated that the reaction quantitatively proceeded and a bis[di(fluorosulfonyl)imide]zinc salt was obtained ($^{19}$F-NMR (CD$_3$CN): δ56.0).

Synthesis Example 18-2

Synthesis of Onium Salt (Cation Exchange)

The reaction solution was transferred to a 5 L separatory funnel and an aqueous solution prepared by dissolving 308.68 g (2.24 mol) of a hydrochloride of triethylamine in 214 g of distilled water was added and mixed, and then the aqueous phase was removed. Furthermore, 214 g of distilled water was added and mixed, and then a liquid separating operation of removing the aqueous phase was repeatedly carried out four times. A part of the resulting organic phase was dried and then analyzed by $^{19}$F-NMR and $^{1}$H-NMR. The results indicated that a di(fluorosulfonyl)imidetriethylammonium salt was obtained (yield: 170.18 g (0.60 mol), $^{19}$F-NMR (CD$_3$CN): δ56.0, $^{1}$H-NMR (CD$_3$CN): δ3.1 (6H), 1.2 (9H)).

Synthesis Example 18-3

Synthesis of Lithium Salt (Cation Exchange)

Furthermore, a butyl acetate solution of the resulting di(fluorosulfonyl)imidetriethylammonium salt was transferred to a 5 L separatory funnel and an aqueous solution prepared by dissolving 75.88 g (1.81 mol) of lithium hydroxide monohydrate in 455 g of distilled water was added and mixed, and then the aqueous phase was removed by a liquid separating operation. The resulting organic phase was evaporated to dryness to obtain a lithium salt of di(fluorosulfonyl)imide (yield: 90.20 g (0.48 mol)). Analysis by $^{19}$F-NMR and $^{1}$H-NMR indicated that the objective product was produced since a peak attributed to triethylammonium disappeared.

$^{19}$F-NMR (CD$_3$CN): δ56.0

Synthesis Example 19

Synthesis Example 19-1

Synthesis of Zinc Salt of Di(fluorosulfonyl)imide

In a 100 ml reaction vessel, 2.00 g (9.3 mmol) of di(chlorosulfonyl)imide and 18 g of valeronitrile were charged, followed by stirring. Into the reaction vessel, 1.01 g (9.8 mmol) of ZnF$_2$ was added, followed by conducting a reaction at room temperature (25° C.) for 3 hours.

The resulting reaction solution was analyzed by $^{19}$F-NMR in the same manner as in Synthesis Example 3. Thus, the results indicated that the reaction quantitatively proceeded and a bis[di(fluorosulfonyl)imide]zinc salt was obtained ($^{19}$F-NMR (CD$_3$CN): δ56.0).

Synthesis Example 19-2

Synthesis of Onium Salt

The reaction solution was transferred to a 100 ml separatory funnel and an aqueous solution prepared by dissolving 2.57 g (18.7 mmol) of a hydrochloride of triethylamine in 1.8 g of distilled water was added and mixed, and then the aqueous phase was removed by a liquid separating operation. Furthermore, 1.8 g of distilled water was added and mixed, and then the aqueous phase was removed. The liquid separating operation of was repeatedly carried out four times. A part of the resulting organic phase was dried and then analyzed by $^{19}$F-NMR. The results indicated that a triethylammonium salt of di(fluorosulfonyl)imide was obtained (yield: 2.02 g (7.2 mmol), $^{19}$F-NMR (CD$_3$CN): δ56.0, $^{1}$H-NMR (CD$_3$CN): δ3.1 (6H), 1.2 (9H)).

Synthesis Example 19-3

Synthesis of Lithium Salt

Furthermore, the resulting valeronitrile solution of a triethylammonium salt of di(fluorosulfonyl)imide was transferred to a 100 ml separatory funnel and an aqueous solution prepared by dissolving 0.91 g (21.6 mmol) of lithium hydroxide monohydrate in 5.5 g of distilled water was added and mixed. The aqueous phase was removed by a liquid separating operation. The same operation was repeatedly carried out twice. The resulting organic phase was evaporated to dryness to obtain of a lithium salt of di(fluorosulfonyl)imide (yield: 0.75 g (4.0 mmol)). Analysis by $^{19}$F-NMR and $^{1}$H-NMR indicated that the objective product was obtained since a peak attributed to triethylammonium disappeared.

$^{19}$F-NMR (CD$_3$CN): δ56.0

As is apparent from the results of Synthesis Examples 18 and 19, each step can be carried out without changing the solvent and the metal salt produced as by-products are easily removed by washing with water and thus the objective compound is efficiently obtained.

Synthesis Example 20

Synthesis of Di(fluorosulfonyl)imide Lithium Salt

A solution (1688 g, 0.46 mol) having a concentration of 7.7% prepared by dissolving triethylammonium di(fluorosulfonyl)imide obtained by the same manner as in Synthesis Example 19 in butyl acetate was weighed and then charged in a 3 L separatory funnel. Into the separatory funnel, a solution prepared by dissolving 58 g (1.38 mol) of lithium hydroxide in 348 g of ultra-pure water was added and mixed, and then the aqueous phase was removed. Analysis by $^{19}$F-NMR and $^1$H-NMR indicated that the objective product was obtained since a peak attributed to triethylammonium disappeared.

The solvent was evaporated and dried by heating the reaction solution to 50° C. and then the reaction solution was dried under reduced pressure to obtain lithium di(fluorosulfonyl) imide (80 g (0.43 mol)).

Synthesis Example 21

Synthesis of Di(chlorosulfonyl)imide

In a 500 ml reaction vessel equipped with a stirrer, a thermometer and a reflux apparatus, 48.5 g (0.5 mol) of amidosulfuric acid, 178.5 g of thionyl chloride and 58.3 g (0.5 mol) of chlorosulfonic acid were charged and the mixed solution was reacted under stirring at 70° C. for 4 hours, and then reacted at 130° C. for 20 hours. After the completion of the reaction, the reflux apparatus was removed from the reaction vessel and distillation under reduced pressure was carried out to give a colorless transparent liquid as a fraction at 104° C. to 105° C. (yield (amount): 102.7 g, 0.48 mol, yield (percentage): 96%).

Identification by IR (Varian 2000 FT-IR, manufactured by Varian, Inc., liquid membrane technique) indicated that the product was di(chlorosulfonyl)imide.
IR (neat): vs(N—H) 3155, vas(S—O) 1433, 1428, vs(S—O) 1183, vs(N—S) 824 cm$^{-1}$ Synthesis Example 22

Synthesis of Bis[di(fluorosulfonyl)imide]zinc Salt

In a 20 ml reaction vessel, 0.50 g (2.01 mmol) of di(chlorosulfonyl)imide obtained in Synthesis Example 21 and 4.5 g of butyl acetate were added, followed by stirring. Into the reaction vessel, 0.25 g (2.5 mmol) of $ZnF_2$ was added, followed by conducting a reaction at room temperature (25° C.) for 3 hours and $^{19}$F-NMR analysis was carried out. A peak area of the resulting chart was measured and the rate of conversion from chlorine into fluorine was determined. Thus, the results indicated that the reaction quantitatively proceeded and a bis[di(fluorosulfonyl)imide]zinc salt was obtained.
$^{19}$F-NMR (CD$_3$CN): δ56.0

Synthesis Example 23

Synthesis of Onium Salt and Lithium Salt

In a 20 ml reaction vessel, a reaction solution containing the bis[di(fluorosulfonyl)imide]zinc salt obtained in Synthesis Example 22 was charged and a solution prepared by dissolving 0.53 g (4.7 mmol) of 1,4-diazobicyclo[2.2.2]octane in 5 g of butyl acetate was added while mixing. After stirring the mixed solution at room temperature (25° C.), the precipitated white solid was collected by filtration. The resulting solid was dissolved in deuterated DMSO and analyzed by $^1$H-NMR and $^{19}$F-NMR. It was found that 1,4-diazobicyclo [2.2.2]octane di(fluorosulfonyl)imide was obtained.

The resulting solid (0.35 g, 1.2 mmol) was mixed with an aqueous solution prepared by dissolving 0.15 g (3.6 mmol) of lithium hydroxide monohydrate in 2 g of distilled water. The cation exchange reaction proceeded, and lithium di(fluorosulfonyl)imide was obtained.

Synthesis Example 24

Synthesis Example 24-1

Synthesis of Onium Salt of Chlorosulfonylimide

In a 20 ml reaction vessel, 2.09 g (9.8 mmol) of di(chlorosulfonyl)imide obtained in Synthesis Example 2 and 4.2 g of butyl acetate were added, followed by stirring. Into the reaction vessel, 0.99 g (9.8 mmol) of triethylamine was added, followed by stirring at room temperature (25° C.) for 1 hour. The resulting reaction solution was analyzed by $^1$H-NMR ("Model Unity plus 400", manufactured by Varian, Inc., internal standard substance: tetramethylsilane, integration time: 32), and it was found that triethylammonium di(chlorosulfonyl)imide was obtained. $^1$H-NMR (CD$_3$CN): δ3.1 (6H), 1.2 (t, 9H)

Synthesis Example 24-2

Synthesis of Onium Salt of Fluorosulfonylimide

To a solution of an onium salt of chlorosulfonylimide obtained in Synthesis Example 24-1, 1.02 g (9.9 mmol) of $ZnF_2$ was added, followed by conducting a reaction at room temperature (25° C.) for 3 hours. The reaction solution was transferred to a 100 ml separatory funnel and then diluted with 12.5 g of butyl acetate. Then, a liquid separating operation of adding 1.9 g of distilled water, mixing and removing the aqueous phase was carried out four times. The product was analyzed by $^{19}$F-NMR ("Model Unity plus 400", manufactured by Varian, Inc., internal standard substance: trifluoromethylbenzene, integration time: 32) and $^1$H-NMR (in the same manner as in Synthesis Example 24-1) and a peak area of the resulting chart was measured, and then the rate of conversion from chlorine into fluorine was determined. The results indicated that triethylammonium di(fluorosulfonyl) imide was obtained (yield (amount): 1.83 g, 6.5 mmol). $^{19}$F-NMR (CD$_3$CN): δ56.0
$^1$H-NMR (CD$_3$CN): δ3.1 (6H), 1.2 (9H)

Synthesis Example 24-3

Synthesis of Lithium Salt (Cation Exchange Reaction)

To a 100 ml separatory funnel, a solution containing triethylammonium di(fluorosulfonyl)imide obtained in Synthesis Example 3-2 was charged and an aqueous solution prepared by dissolving 0.82 g (19.5 mmol) of lithium hydroxide monohydrate in 4.92 g of distilled water was added and mixed. The aqueous phase was removed by a liquid separating operation. The same operation was repeatedly carried out twice. The solvent was evaporated from the resulting organic phase, followed by drying to obtain a product. $^1$H-NMR analysis indicated that lithium di(fluorosulfonyl)imide was obtained (yield (amount): 0.79 g, 4.2 mmol) since a peak attributed to triethylammonium disappeared.

Synthesis Example 25

Synthesis Example 25-1

Synthesis of Onium Salt of Di(chlorosulfonyl)imide

In a 50 ml reaction vessel, 2.00 g (9.3 mmol) of di(chlorosulfonyl)imide obtained in Synthesis Example 2 and 18 g of valeronitrile were added, followed by stirring. Into the reaction vessel, 0.95 g (9.4 mmol) of triethylamine was added, followed by further stirring. Analysis of the resulting reaction solution by $^1$H-NMR indicated that triethylammonium di(chlorosulfonyl)imide was obtained.

$^1$H-NMR (CD$_3$CN): δ3.1 (6H), 1.2 (9H)

Synthesis Example 25-2

Synthesis of Onium Salt of Fluorosulfonylimide

To the reaction solution obtained in Synthesis Example 25-1, 0.97 g (9.4 mmol) of ZnF$_2$ was added, followed by conducting a reaction at room temperature (25° C.) for 3 hours. The reaction solution was transferred to a 100 ml separatory funnel and 1.9 g of water was added and mixed, and then the aqueous phase was removed by a liquid separating operation. This operation was carried out four times and the resulting organic phase was analyzed by $^{19}$F-NMR and $^1$H-NMR. The results indicated that triethylammonium di(fluorosulfonyl)imide was obtained (yield (amount): 1.30 g, 4.6 mmol).

$^{19}$F-NMR (CD$_3$CN): δ56.0
$^1$H-NMR (CD$_3$CN): δ3.1 (6H), 1.2 (9H)

Synthesis Example 25-3

Synthesis of Lithium Salt (Cation Exchange Reaction)

To a 100 ml separatory funnel, the organic phase obtained in Synthesis Example 25-2 was transferred and an aqueous solution prepared by dissolving 0.58 g (13.8 mmol) of lithium hydroxide monohydrate in 3.5 g of distilled water was added and mixed. Thereafter, the aqueous phase was removed by a liquid separating operation. The solvent was evaporated from the resulting organic phase, followed by drying to obtain a product. $^1$H-NMR analysis indicated that lithium di(fluorosulfonyl)imide was produced (yield (amount): 0.77 g, 4.1 mmol) since a peak attributed to triethylammonium disappeared.

$^{19}$F-NMR (CD$_3$CN): δ56.0

As is apparent from the results of Synthesis Examples 24 and 25, according to the method of the present invention, chlorosulfonylimide is efficiently fluorinated by using a fluorinating agent which is cheaper than the conventional ones. The method of the present invention is excellent in operability since the fluorination and the cation exchange reaction can be carried out using the same reaction solvent, and also purification may be carried out only by a liquid separating operation.

Synthesis Example 26

Synthesis Example 26-1

Synthesis of Onium Salt

In a 50 ml reaction vessel, 2.00 g (8.1 mmol) of N-chlorosulfonyl-N-(trifluoromethylsulfonyl)imide obtained in Synthesis Example 15 and 18 g of butyl acetate were added, followed by stirring. Into the reaction vessel, 0.82 g (8.1 mmol) of triethylamine was added, followed by stirring at room temperature (25° C.) for 1 hour. The resulting reaction solution was analyzed by $^1$H-NMR, and it was found that triethylammonium N-(chlorosulfonyl)-N-(trifluoromethylsulfonyl)imide was obtained.

$^1$H-NMR (CD$_3$CN): δ3.1 (6H), 1.2 (9H)

Synthesis Example 26-2

Synthesis of Onium Salt of Fluorosulfonylimide

To the reaction solution obtained in Synthesis Example 26-1, 0.88 g (8.5 mmol) of ZnF$_2$ was added, followed by conducting a reaction at room temperature (25° C.) for 3 hours. The reaction solution was transferred to a 100 ml separatory funnel and 1.9 g of water was added and mixed, and then the aqueous phase was removed. The a liquid separating operation was repeatedly carried out four times. The resulting reaction solution was analyzed by $^{19}$F-NMR and $^1$H-NMR. The results indicated that triethylammonium-N-(fluorosulfonyl)-N-(trifluoromethylsulfonyl)imide was obtained (yield (amount): 1.63 g, 4.9 mmol).

$^1$H-NMR (CD$_3$CN): δ3.1 (6H), 1.2 (9H)

Synthesis Example 27

Synthesis Example 27-1

Synthesis of Onium Salt

In a 50 ml reaction vessel, 2.00 g (9.3 mmol) of di(chlorosulfonyl)imide obtained in Synthesis Example 2 and 18 g of butyl acetate were added, followed by stirring. Into the reaction vessel, 0.94 g (9.3 mmol) of triethylamine was added, and the reaction mixture was stirred. Analysis of the resulting reaction solution by $^1$H-NMR indicated that triethylammonium di(chlorosulfonyl)imide was produced (yield (amount): 1.47 g, 5.2 mmol).

$^1$H-NMR (CD$_3$CN): δ3.1 (6H), 1.2 (9H)

Synthesis Example 27-2

Synthesis of Onium Salt of Fluorosulfonylimide

To the reaction solution obtained in Synthesis Example 27-1, 1.00 g (0.98 mmol) of CuF$_2$ was added, followed by conducting a reaction at room temperature (25° C.) for 3 hours.

The reaction solution was transferred to a 100 ml separatory funnel and a liquid separating operation of adding 1.9 g of distilled water, mixing and removing the aqueous phase was carried out four times. Butyl acetate was distilled off from the resulting organic phase to obtain an oily yellow product. Analysis of the product by $^{19}$F-NMR and $^1$H-NMR indicated that triethylammonium di(fluorosulfonyl)imide was obtained (yield (amount): 1.47 g, 5.2 mmol).

$^{19}$F-NMR (CD$_3$CN): δ56.0
$^1$H-NMR (CD$_3$CN): δ3.1 (6H), 1.2 (9H)

Synthesis Example 28

Synthesis Example 28-1

Synthesis of Onium Salt

In a 50 ml reaction vessel, 2.00 g (9.3 mmol) of di(chlorosulfonyl)imide and 18 g of butyl acetate were added, followed by stirring. Into the reaction vessel, 0.94 g (9.3 mmol) of triethylamine was added, followed by stirring. Analysis of the resulting reaction solution by $^1$H-NMR indicated that triethylammonium di(chlorosulfonyl)imide was obtained.

Synthesis Example 28-2

Synthesis of Onium Salt of Fluorosulfonylimide

To the reaction solution obtained in Synthesis Example 28-1, 1.66 g (6.2 mmol) of $BiF_3$ was added, followed by conducting a reaction at room temperature (25° C.) for 3 hours.

The reaction solution was transferred to a 100 ml separatory funnel and a liquid separating operation of adding 1.9 g of distilled water, mixing and removing the aqueous phase was carried out four times. The resulting organic phase was analyzed by $^{19}$F-NMR and $^1$H-NMR. The results indicated that triethylammonium di(fluorosulfonyl)imide was obtained (yield (amount): 1.36 g, 4.8 mmol).

$^{19}$F-NMR ($CD_3CN$): δ56.0
$^1$H-NMR ($CD_3CN$): δ3.1 (6H), 1.2 (9H)

As is apparent from the results of Synthesis Examples 27 and 28, even when using a fluoride compound containing elements of Group 11 to Group 15 and Period 4 to Period 6 (excluding arsenic and antimony) other than Zn, fluorination of an organic salt of chlorosulfonylimide rapidly proceeds to efficiently obtain a fluorosulfonylimide salt without producing by-products.

Synthesis Example 29

Synthesis of Lithium Salt

A solution (1688 g, 0.46 mol) having a concentration of 7.7% prepared by dissolving triethylammonium di(fluorosulfonyl)imide obtained in the same manner as in Synthesis Example 24-2 in butyl acetate was weighed and then charged in a 3 L separatory funnel. Into the separatory funnel, a solution prepared by dissolving 58 g (1.38 mol) of lithium hydroxide in 348 g of ultrapure water was added and mixed, and then the aqueous phase was removed. Analysis by $^{19}$F-NMR and $^1$H-NMR indicated that the objective product was obtained since a peak attributed to triethylammonium disappeared.

Then, the reaction solution was dried under reduced pressure at 50° C. to obtain 80 g (0.43 mol) of lithium di(fluorosulfonyl)imide.

Synthesis Example 30

Synthesis Example 30-1

Synthesis of Onium Salt of Chlorosulfonylimide

In a 20 ml reaction vessel, 2.09 g (9.8 mmol) of di(chlorosulfonyl)imide obtained in Synthesis Example 2 and 4.2 g of butyl acetate were added, followed by stirring. Into the reaction vessel, 1.35 g (9.8 mmol) of triethylamine hydrochloride was added, followed by stirring at room temperature (25° C.) for 1 hour. Analysis of the resulting reaction solution by $^1$H-NMR under the same conditions as in Synthesis Example 3-1 indicated that triethylammonium di(chlorosulfonyl)imide was obtained.

$^1$H-NMR ($CD_3CN$): δ3.1 (6H), 1.2 (9H)

Synthesis Example 30-2

Synthesis of Onium Salt of Fluorosulfonylimide

To a solution of an onium salt of chlorosulfonylimide obtained in Synthesis Example 30-1, 1.02 g (9.9 mmol) of $ZnF_2$ was added, followed by conducting a reaction at room temperature (25° C.) for 3 hours. The reaction solution was transferred to a 100 ml separatory funnel and then diluted with 12.5 g of butyl acetate. Then, a liquid separating operation of adding 1.9 g of distilled water, mixing and removing the aqueous phase was carried out four times. Under the same conditions as in Synthesis Example 24-2, the product was analyzed by $^{19}$F-NMR and $^1$H-NMR (in the same manner as in Synthesis Example 3-1), and then a peak area of the resulting chart was measured and the rate of conversion from chlorine into fluorine was determined. The results indicated that triethylammonium di(fluorosulfonyl)imide was obtained (yield (amount): 1.82 g, 6.4 mmol).

$^{19}$F-NMR ($CD_3CN$): δ56.0

Synthesis Example 31

In a 50 ml reaction vessel, 3.01 g (14.1 mmol) of di(chlorosulfonyl)imide and 27.09 g of valeronitrile were charged, followed by stirring. Into the reaction vessel, 1.53 g (14.8 mmol) of $ZnF_2$ was added, followed by a reaction at room temperature (25° C.) for 4 hours. The resulting reaction solution was analyzed by $^{19}$F-NMR in the same manner as in Synthesis Example 3. The results indicated that the reaction quantitatively proceeded and a bis[di(fluorosulfonyl)imide] zinc salt was obtained.

$^{19}$F-NMR ($CD_3CN$): δ56.0

The reaction solution was transferred to a 50 ml separatory funnel and an aqueous solution prepared by dissolving 0.60 g (14.1 mmol) of lithium chloride in 2.71 g of distilled water was added and mixed, and then the aqueous phase was removed. This liquid separating operation was repeated four times. The resulting organic phase was dried and analyzed by $^{19}$F-NMR and ICP emission analysis ("Model ICPE-9000", manufactured by Shimadzu Corporation). The results indicated that a lithium salt of di(fluorosulfonyl)imide was obtained (yield (amount): 1.29 g, 6.4 mmol) since a peak attributed to a Zn ion disappeared and a peak attributed to an Li ion existed.

$^{19}$F-NMR ($CD_3CN$): δ56.0

INDUSTRIAL APPLICABILITY

According to the present invention, production of by-products are suppressed without using an expensive fluorinating agent having high toxicity such as antimony (Sb) or arsenic (As), and also N-(fluorosulfonyl)-N-(fluoroalkylsulfonyl)imide, di(fluorosulfonyl)imide and organic salts thereof and metal salts thereof is obtained efficiently when compared with a conventional method. The fluorosulfonylimides obtained by the present method are thought to be suited for use as a material of an ion conductor constituting electrochemical devices such as a primary battery, batteries having a charge/discharge mechanism such as a lithium (ion) secondary battery and a fuel cell, an electrolytic capacitor, an electric double layer capacitor, a solar battery and an electrochromic display device.

This application is based on Japanese Patent applications No. 2008-93240 filed on Mar. 31, 2008, No. 2009-12344, No. 2009-12345, No. 2009-12346 filed on Jan. 22, 2009, the contents of which are hereby incorporated by reference.

The invention claimed is:

1. A method for producing a fluorosulfonylimide salt comprising
reacting a fluoride compound containing at least one element selected from the group consisting of di- or higher polyvalent elements of Group 11 to Group 15 and Period 4 to Period 6 (excluding arsenic and antimony) with a compound represented by the following general formula (I) to obtain a fluorosulfonylimide salt represented by the general formula (II):

[Chemical Formula 1]

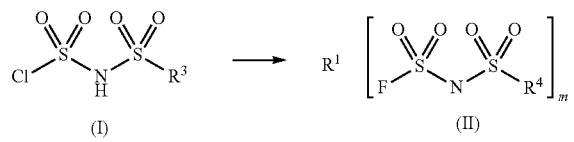

wherein $R^1$ denotes at least one element selected from the group consisting of di- or higher polyvalent elements of Group 11 to Group 15 and Period 4 to Period 6 (excluding arsenic and antimony); $R^3$ denotes fluorine, chlorine or a fluorinated alkyl group having 1 to 6 carbon atoms; $R^4$ denotes fluorine or a fluorinated alkyl group having 1 to 6 carbon atoms; and m denotes an integer of 2 or 3.

2. The method for producing a fluorosulfonylimide salt according to claim 1, further comprising a step of cationic-exchanging reaction of the compound of the general formula (II) obtained by the method according to claim 1 to obtain a fluorosulfonylimide salt represented by the following general formula (III):

[Chemical Formula 2]

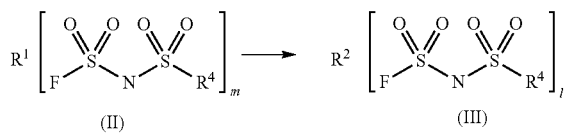

wherein $R^1$ denotes at least one element selected from the group consisting of di- or higher polyvalent elements of Group 11 to Group 15 and Period 4 to Period 6 (excluding arsenic and antimony); $R^2$ denotes $H^+$ or a metal ion other than $R^1$; $R^4$ denotes fluorine or a fluorinated alkyl group having 1 to 6 carbon atoms; m denotes an integer of 2 or 3; and l denotes an integer of 1 to 3.

3. The method for producing a fluorosulfonylimide salt according to claim 1 or 2, further comprising steps of;
reacting the compound of the general formula (II) obtained by the method according to claim 1 with an organic compound containing an onium cation to give an organic salt of fluorosulfonylimide represented by the following general formula (VI), and
exchanging a cation of the organic salt of the fluorosulfonylimide to obtain a fluorosulfonylimide salt represented by the general formula (III):

[Chemical Formula 3]

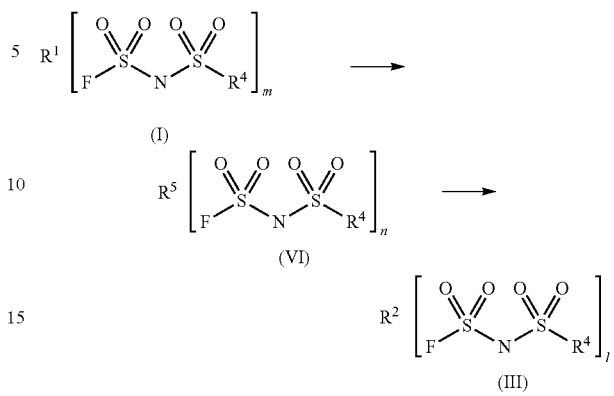

wherein $R^1$ denotes at least one element selected from the group consisting of di- or higher polyvalent elements of Group 11 to Group 15 and Period 4 to Period 6 (excluding arsenic and antimony); $R^2$ denotes $H^+$ or a metal ion other than $R^1$; $R^4$ denotes fluorine or a fluorinated alkyl group having 1 to 6 carbon atoms; $R^5$ denotes an onium cation; l denotes an integer of 1 to 3; m denotes an integer of 2 or 3; and n corresponds to a valence of the onium cation $R^5$ and denotes an integer of 1 to 3.

4. The method for producing a fluorosulfonylimide salt according to claim 1, further comprising a step of reacting the compound of the general formula (II) obtained by the method according to claim 1 with an organic compound containing an onium cation to obtain a fluorosulfonylimide salt represented by the following general formula (VI):

[Chemical Formula 4]

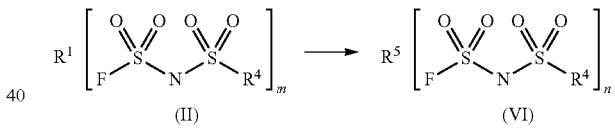

wherein $R^1$ denotes at least one element selected from the group consisting of di- or higher polyvalent elements of Group 11 to Group 15 and Period 4 to Period 6 (excluding arsenic and antimony); $R^4$ denotes fluorine or a fluorinated alkyl group having 1 to 6 carbon atoms; $R^5$ denotes an onium cation; m denotes an integer of 2 or 3; and n corresponds to a valence of the onium organic cation $R^5$ and denotes an integer of 1 to 3.

5. The method for producing a fluorosulfonylimide salt according to claim 2, further comprising a step of reacting the compound of the general formula (III) obtained by the method according to claim 2 with an organic compound containing an onium cation to give a fluorosulfonylimide salt represented by the general formula (VI):

[Chemical Formula 5]

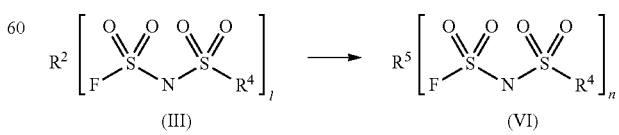

wherein $R^2$ denotes $H^+$ or a metal ion other than $R^1$; $R^4$ denotes fluorine or a fluorinated alkyl group having 1 to 6 carbon atoms; $R^5$ denotes an onium cation; l denotes an integer of 1 to 3; and n corresponds to a valence of the onium organic cation $R^5$ and denotes an integer of 1 to 3.

6. A method for producing a fluorosulfonylimide salt, which is represented by the following scheme, comprising steps of:
reacting a compound represented by the general formula (I) shown in the following scheme with an organic compound containing an onium cation to give an organic salt of chlorosulfonylimide represented by the general formula (VIII); and
reacting the organic salt of chlorosulfonylimide with a fluoride compound containing at least one element selected from the group consisting of di- or higher polyvalent elements of Group 11 to Group 15 and Period 4 to Period 6 (excluding arsenic and antimony) to obtain a compound represented by the general formula (VI), in this order:
[Chemical Formula 6]

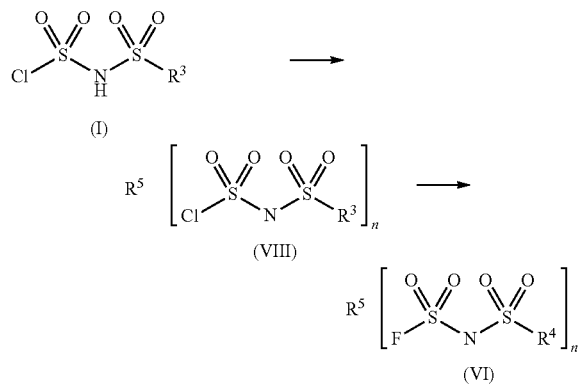

wherein $R^3$ denotes fluorine, chlorine or a fluorinated alkyl group having 1 to 6 carbon atoms; $R^4$ denotes fluorine or a fluorinated alkyl group having 1 to 6 carbon atoms; $R^5$ is an onium cation; and n corresponds to a valence of the onium cation $R^5$ and denotes an integer of 1 to 3.

7. The method for producing a fluorosulfonylimide salt according to claim 6, further comprising the step of reacting the compound represented by the general formula (VI) obtained by the method according to claim 6 with an alkali metal salt to obtain a compound represented by the following general formula (III):
[Chemical Formula 7]

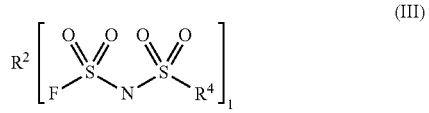

wherein $R^2$ denotes an alkali metal; $R^4$ denotes fluorine or a fluorinated alkyl group having 1 to 6 carbon atoms; and l denotes 1.

8. The method for producing a fluorosulfonylimide salt according to any one of claims 1, 2 or 4 to 7, wherein the fluoride compound contains at least one element selected from the group consisting of Cu, Zn and Bi.

9. The method for producing a fluorosulfonylimide salt according to any one of claims 1, 2 or 4 to 7, wherein $R^3$ is chlorine in the general formula (I) and $R^4$ is fluorine in the general formula (II) and the general formula (III).

10. The method for producing a fluorosulfonylimide salt according to claim 2 or 5, wherein the metal ion represented by $R^2$ in the general formula (III) is an alkali metal.

11. The method for producing a fluorosulfonylimide salt according to claim 1, wherein the compound represented by the general formula (I) is obtainable by using cyanogen chloride as a starting material.

12. The method for producing a fluorosulfonylimide salt according to claim 1, wherein the compound represented by the general formula (I) is obtainable by using amidosulfuric acid as a starting material.

13. The method for producing a fluorosulfonylimide salt according to claim 3, further comprising a step of reacting the compound of the general formula (III) obtained by the method according to claim 3 with an organic compound containing an onium cation to give a fluorosulfonylimide salt represented by the general formula (VI):
[Chemical Formula 5]

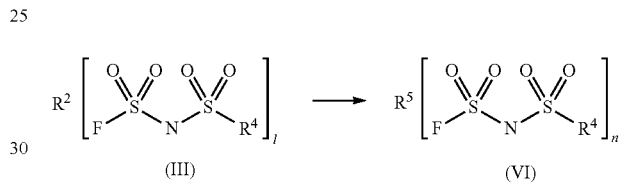

wherein $R^2$ denotes $H^+$ or a metal ion other than $R^1$; $R^4$ denotes fluorine or a fluorinated alkyl group having 1 to 6 carbon atoms; $R^5$ denotes an onium cation; l denotes an integer of 1 to 3; and n corresponds to a valence of the onium organic cation $R^5$ and denotes an integer of 1 to 3.

14. The method for producing a fluorosulfonylimide salt according to claim 3, wherein the fluoride compound contains at least one element selected from the group consisting of Cu, Zn and Bi.

15. The method for producing a fluorosulfonylimide salt according to claim 13, wherein the fluoride compound contains at least one element selected from the group consisting of Cu, Zn and Bi.

16. The method for producing a fluorosulfonylimide salt according to claim 3, wherein $R^3$ is chlorine in the general formula (I) and $R^4$ is fluorine in the general formula (II) and the general formula (III).

17. The method for producing a fluorosulfonylimide salt according to claim 13, wherein $R^3$ is chlorine in the general formula (I) and $R^4$ is fluorine in the general formula (II) and the general formula (III).

18. The method for producing a fluorosulfonylimide salt according to claim 8, wherein $R^3$ is chlorine in the general formula (I) and $R^4$ is fluorine in the general formula (II) and the general formula (III).

19. The method for producing a fluorosulfonylimide salt according to claim 3, wherein the metal ion represented by $R^2$ in the general formula (III) is an alkali metal.

* * * * *